United States Patent [19]
Reha-Krantz et al.

[11] Patent Number: 5,928,919
[45] Date of Patent: Jul. 27, 1999

[54] VARIANT DNA POLYMERASES

[75] Inventors: Linda J. Reha-Krantz, Edmonton, Canada; Myron F. Goodman, LaCanada, Calif.

[73] Assignees: The University of Southern California, Los Angeles, Calif.; The University of Alberta, Edmonton, Canada

[21] Appl. No.: 08/465,994

[22] Filed: Jun. 6, 1995

Related U.S. Application Data

[62] Division of application No. 08/101,593, Aug. 2, 1993, Pat. No. 5,547,859.

[51] Int. Cl.$^6$ ............................................. C12N 9/00
[52] U.S. Cl. ............................. 435/183; 935/77; 935/82; 935/11
[58] Field of Search ..................... 530/350, 358; 935/77, 82, 11; 435/183

[56] References Cited

PUBLICATIONS

Reha–Krantz et al., Proc. Natl. Acad. Sci., 88:2417–2421, Mar. 1991.

Reha–Krantz et al., J. Mol. Biol., 189(2):262–272, May 1986.

Reha–Krantz, L.J., et al., "Bacteriophage T4 DNA Polymerase Mutations That Confer Sensitivity to the PP; Analog Phosphonoacetic Acid", J. Virol., 67(1):60–66 (1993).

*Primary Examiner*—Scott W. Houtteman
*Attorney, Agent, or Firm*—Fulbright & Jaworski, LLP

[57] ABSTRACT

Variant family B DNA polymerases, examples of which have reduced or no 3'→5' exonuclease activity. These variant polymerases have utility as DNA sequencing polymerases.

6 Claims, 6 Drawing Sheets

NUCLEOTIDE STRUCTURES

2'-DEOXYRIBONUCLEOSIDE TRIPHOSPHATES (dNTPs)

2',3'-DIDEOXYRIBONUCLEOSIDE TRIPHOSPHATES (ddNTPs)

3'-AMINO-2',3' DIDEOXYRIBONUCLEOSIDE TRIPHOSPHATES (3'-NH₂ ddNTPs)

ARABINONUCLEOSIDE TRIPHOSPHATES (araNTPs)

ized by an asterisk (*). The protein sequence of wild type
VARIANT DNA POLYMERASES

REFERENCE TO RELATED APPLICATIONS

This is a divisional of application Ser. No. 08/101,593, filed Aug. 2, 1993, which issued as U.S. Pat. No. 5,547,859 on Aug. 20, 1996. In addition, this divisional is related to a divisional application, Ser. No. 08/465,995, filed Jun. 6, 1995 now U.S. Pat. No. 5,660,980.

BACKGROUND OF THE INVENTION

The present invention relates to modifications of the DNA sequencing method developed by F. Sanger (Sanger, F., Nicklen, S., Coulson, A. R. (1977) *Proc. Natl. Acac. Sci. U.S.A.* 74, 5463–5467) as well as to novel enzymes which can be used for DNA sequencing. The Sanger sequencing method is based on in vitro DNA synthesis reactions in the presence of a primed DNA template, 2'-deoxyribonucleoside triphosphates (dNTPs, see FIG. 1), and 2',3'-dideoxyribonucleoside triphosphates (ddNTPs, FIG. 1). The latter, when incorporated by a DNA polymerase into a polynucleotide chain, terminate further chain elongation. The DNA products are thus a series of polynucleotide chains complementary to the template and terminated with specific dideoxynucleotides. The DNA sequencing products can be separated by size and the pattern of the products gives the DNA sequence.

In principle, DNA polymerases from a variety of organisms and a variety of chain-terminating nucleotides should be useful to sequence DNA. In practice, few DNA polymerases and chain-terminating nucleotides have been found to be suitable for this purpose. As an example of a DNA sequencing polymerase, the development of bacteriophage T7 DNA polymerase, Sequenace™, will be reviewed (Tabor, S., and Richardson, C. C. (1990) *J. Biol. Chem.* 265, 8322–8328). In order to obtain an unambiguous DNA sequence it is necessary that the majority of sequencing products terminate with a dideoxynucleotide and that all the sequencing products are represented equally. Two phage T7 DNA polymerase activities degrade DNA sequencing products and, thus, these activities must be eliminated in order to prevent degradation of dideoxynucleotide-terminated sequencing products. One activity, 3'→5' exonuclease activity, was removed by constructing an exonuclease deficient variant of T7 DNA polymerase. T7 DNA polymerase also has pyrophosphorolytic activity which can degrade the sequencing products. Pyrophosphatase was added to degrade pyrophosphate produced in the DNA sequencing reactions; without pyrophosphate, there is no pyrophosphorolysis. A further refinement of the sequencing reactions was to use $Mn^{2+}$ in place of $Mg^{2+}$ which resulted in a more equal distribution of reaction products. Although this brier review of the development of T7 DNA polymerase into a sequencing polymerase is a simplification, the review illustrates the point that modification of a natural DNA polymerase as well as development of reaction conditions is required in order to obtain high quality DNA sequence information using the chain-terminating sequencing method.

Optimal DNA sequencing conditions using the chain-terminating method have not yet been achieved. Ambiguous sequencing information is still observed which necessitates determining the DNA sequence of both DNA strands. Also, the use of $Mn^{2+}$ in place of $Mg^{2+}$ increases the amount of DNA template required for sequencing reactions. Thus it would be advantageous to develop novel methods that would improve or complement existing sequencing procedures.

The wild type T4 DNA polymerase gene has been cloned and the protein product expressed (Lin, T.-C., Rush, J. R., Spicer, E. K., and Konigsberg, W. H. (1987) *Proc. Natl. Acad. Sci. U.S.A.* 84, 7000–7004; U.S. Pat. No. 4,935,361 to Lin et al.) and *E. coli* DNA polymerase II has been cloned and expressed (Bonner, C. A., Hays, S., McEntee, K., and Goodman, M. F. (1990) *Proc. Natl. Acad. Sci. U.S.A.* 87, 7663–7667). Standard oligonucleotide-directed mutagenesis techniques have been used to construct novel forms of T4 DNA polymerase and *E. coli* DNA polymerase II. Thus, the means exist to economically prepare large quantities of wild type and variant T4 DNA polymerase and *E. coli* DNA polymerase II.

Another aspect of the invention is to use genetic analysis to identify DNA polymerases with properties useful for DNA sequencing. T4 DNA polymerase is one of the most extensively genetically characterized DNA polymerases (Reha-Krantz, L. J. (1993) In *Molecular Biology of Bacteriophage T4*, ed. Karam J., American Association for Microbiology, in press); hence, some mutant DNA polymerases already identified may have properties useful for DNA sequencing and new mutants can be isolated directly. A method to isolate novel T4 DNA polymerases with useful DNA sequencing properties would be of additional utility.

SUMMARY OF THE INVENTION

In accordance with aspect of the invention, there are provided novel enzymes which may be used as DNA sequencing polymerases. These enzymes result from genetic mutations of family B DNA polymerases. These mutations eliminate the 3'→5' exonuclease activity of these novel family B DNA polymerases.

In accordance with another aspect of the invention, there are provided methods that enable phage T4 DNA polymerase and *E. coli* DNA polymerase II to be used as DNA sequencing polymerases. DNA polymerase modifications that convert phage T4 DNA polymerase and *E. coli* DNA polymerase II into DNA sequencing polymerases can also be used to similarly modify DNA polymerases having protein sequence homology with these two polymerases. DNA polymerases with protein sequence similarities to T4 DNA polymerase and *E. coli* DNA polymerase II include, but are not limited to, a group of DNA polymerases that are called Family B DNA polymerases (Braithwaite, D. K. and Ito, J. (1993) *Nucl. Acids Res.* 21, 787–802). Of particular relevance are the DNA polymerases from phages T2 and T6 which have extensive protein sequence homology to T4 DNA polymerase. Another extension of methods described here is that DNA polymerases with functional similarities to T4 DNA polymerase and *E. coli* DNA polymerase II may also be used to produce DNA sequence information with the chain-terminating nucleotides and methods disclosed hereinafter.

In accordance with another aspect of this invention there is provided a method to identify DNA polymerase modifications, having one or more specific amino acid substitutions in the polymerase protein sequence, that improve a given DNA polymerase in terms of DNA sequencing applications.

DETAILED DESCRIPTION OF THE INVENTION

Figure 1:
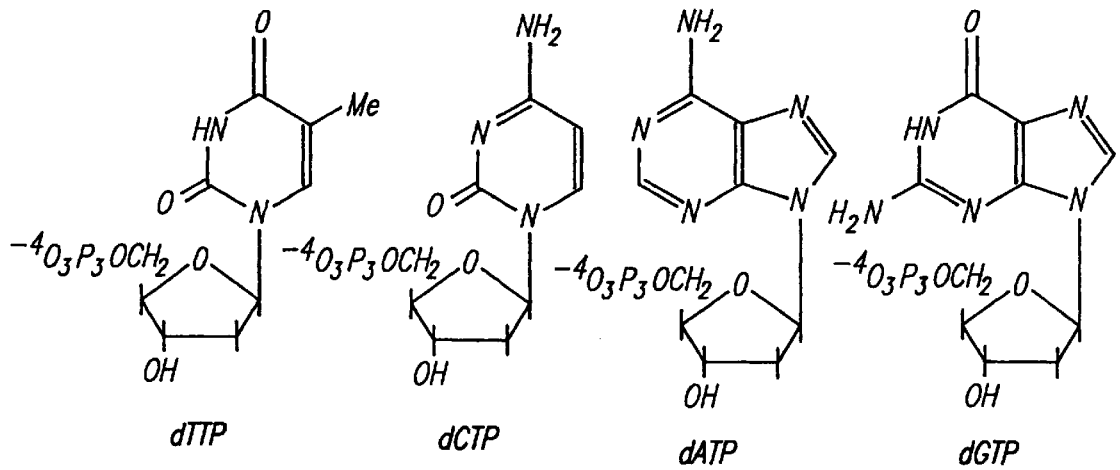
FIG. 1 depicts the structure of standard nucleotides and nucleotide analogs useful in the practice of the invention.
Figure 1:
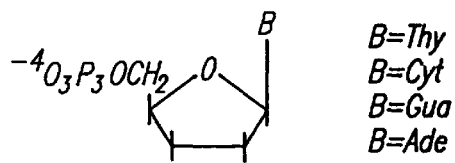
Figure 1:
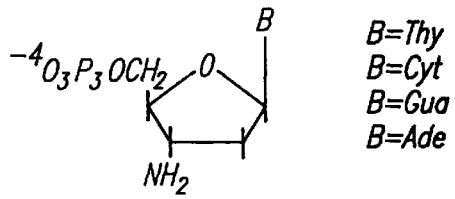
Figure 1:
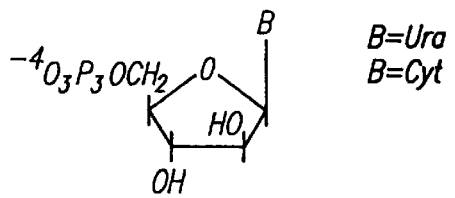
Figure 1:
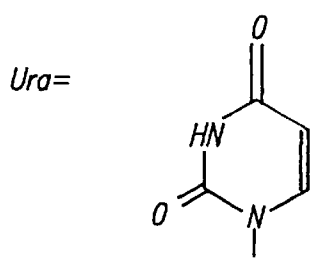

An aspect of the invention, namely to identify modified DNA polymerases with new properties that improve the ability of the modified DNA polymerases to carry out DNA sequencing reactions, is achieved by the design of a new genetic selection strategy that identifies modified DNA polymerases with superior DNA replication activities. The new genetic selection strategy has been designed around the T4 DNA polymerase.

T4 DNA polymerase (SEQ ID NOS: 3 and 4) and *E. coli* DNA polymerase II (SEQ ID NOS: 5 and 6), which have heretofore been unable to be used as sequencing polymerases, can be used as DNA sequencing polymerases in Sanger-type reactions if non-standard or novel combinations of chain-terminating nucleotides are used. Further to this discovery is the finding that inactivation of 3'→5' exonuclease activity in T4 DNA polymerase and *E. coli* DNA polymerase II improves the quality of the DNA sequence information obtained. In a further aspect, additional polymerase modifications have been discovered, which when combined with other modifications that reduce 3'→5' exonuclease activity, have the potential to produce a multiply modified DNA polymerase with advantageous DNA sequencing properties. Due to extensive sequence homology with T4 DNA polymerase, DNA polymerases such as phages T2 (SEQ ID NOS: 1 and 2) and T6 DNA polymerases are particularly suitable in the application of the methods of the invention.

T4 DNA polymerase and *E. coli* DNA polymerase II can be used as effective DNA sequencing polymerases if the arabinonucleotides (FIG. 1), araUTP and araCTP, are used in place of the standard chain-terminating nucleotides ddTTP and ddCTP. The standard purine dideoxynucleotides (FIG. 1), ddATP and ddGTP, are effective chain-terminating nucleotides for T4 DNA polymerase and *E. coli* DNA polymerase II. DNA sequencing reactions for T4 DNA polymerase and *E. coli* DNA polymerase II differ from standard DNA sequencing reactions in that a novel combination of chain-terminating nucleotides is used. Although in principle any chain-terminating nucleotide may be used, DNA polymerases differ markedly in their ability to incorporate these nucleotides into the DNA chain. For T4 DNA polymerase and *E. coli* DNA polymerase II, the low incorporation of ddTTP and ddCTP by these enzymes have prevented the use of these standard chain-terminating nucleotides in sequencing protocols. The discovery that alternative chain-terminating arabinonucleotides, araCTP and araUTP, can be incorporated relatively efficiently by T4 DNA polymerase and *E. coli* DNA polymerase II enables these DNA polymerases to be used as sequencing polymerases. The DNA sequencing method that uses reactions with the novel combinations of chain-terminating nucleotides—araCTP, araUTP, ddATP and ddGTP, is described, hereinbelow, in Method I.

A further discovery is that inactivation or significant reduction of the 3'→5' exonuclease activity of T4 DNA polymerase and *E. coli* DNA polymerase II enhances the quality of DNA sequence information obtained using the Method I sequencing reactions. T4 DNA polymerase 3'→5' exonuclease activity can be significantly reduced by an amino acid substitution including, but not limited to, one or more of the following amino acid substitutions in the enzyme: D112A+E114A, D219A and D324A. In the above nomenclature which is used herein throughout, the single letter code for amino acids is used. The numbers flanked by the single letter codes for amino acids are the codon numbers. For example, D112A+E114A indicates an alanine (A) substitution for aspartate (D) at codon position 112. D112A+E114A indicates two amino acid substitutions in the modified DNA polymerase. To achieve these variants the following mutations were employed: for D112A the A nucleotide at position 335 is replaced with a C nucleotide thereby effecting a change of the D amino acid to an A amino acid, as is known to one of ordinary skill in the art other nucleotide changes are capable of effecting the same change; for E114A the A nucleotide at position 341 is replaced with a C nucleotide, as is known other nucleotide changes can effect the same amino acid change; for D219A the A nucleotide at position 656 is replaced with a C nucleotide, respectively, as is known other nucleotide changes can effect the same amino acid change; and for D324A the A nucleotide at position 971 is replaced with a C nucleotide, as is known other nucleotide changes can effect the same amino acid change. *E. coli* DNA polymerase II 3'→5' exonuclease activity can be significantly reduced by an amino acid substitution including, but not limited to, the following amino acid substitutions: D156A+E158A. To achieve these variants the following mutations were employed: for D156A the A nucleotide at position 467 is replaced with a C nucleotide, as is known other nucleotide changes can effect the same amino acid change; for E158A the A nucleotide at position 473 is replaced with a C nucleotide, as is known other nucleotide changes can effect the same amino acid change. Construction of 3'→5' exonuclease deficient variants of T4 DNA polymerase and *E. coli* DNA polymerase II is achieved by standard oligonucleotide mutagenesis procedures (for example, Kunkle, T. A., Roberts, J. D. and Zakour, R. A. (1987) *Method. Enz.* 154, 367–382).

Another aspect of the invention may be achieved by using chain-terminating nucleotides that are not used in standard DNA sequencing reactions. T4 DNA polymerase and *E. coli* DNA polymerase II may also be used as effective DNA sequencing polymerases if 3'amino-2',3'-dideoxyribonucleotides (3'-NH$_2$dNTPs) (FIG. 1) are used in place of the standard ddNTPs. This sequencing method is described herein below in Method II. Unmodified (wild type) T4 DNA polymerase and 3'→5' exonuclease deficient variants can be used in Method II reactions; the 3'→5' exonuclease deficient variant of *E. coli* DNA polymerase II has also been successfully used in Method II reactions.

The 3'→5' exonuclease deficient form of T4 DNA polymerase can also be used to produce DNA sequence information without nucleotide analogs if the concentration of one of the four standard dNTPs is very low. For example, if the concentrations of dGTP, dCTP and dTTP are at 100 μM and the concentration of dATP is at 0.1 μM to 1 μM then sequencing products are observed that terminate one position before dATP is required for incorporation. With parallel reactions, each with one dNTP present at low concentration and the other three dNTPs present at high concentrations, the DNA sequence can be determined. This sequencing method is referred to hereinafter as Method III.

The third objective, namely to identify variant or modified DNA polymerases with new properties that enable the polymerases to have enhanced sequencing properties, has been achieved by designing a new strategy to select for novel DNA polymerases. The new strategy, a type of genetic selection, was developed for phage T4. The basic strategy begins with a phage T4 strain that has one or more mutations in the DNA polymerase gene which result in a variant (mutant) DNA polymerase which is partially defective in some aspect of DNA replication. Several types of DNA polymerase modifications can reduce the ability of DNA polymerase to replicate DNA efficiently. For example, alterations in the ability of the DNA polymerase to bind DNA template or dNTPs or in the ability of the DNA polymerase to translocate along the DNA template will reduce DNA replication efficiency. For phage T4, DNA polymerase mutants with reduced DNA replication activity can be readily identified. Phage T4 strains with mutant DNA polymerases that are partially defective in DNA replication cannot synthesize DNA if the bacterial host used in the infection contains the optA1 mutation. In other words, the *E. coli* optA1 host restricts growth of T4 strains with mutant DNA polymerases defective in DNA replication activity. The basis of the restriction observed for the *E. coli* optA1 strain is that increased amounts of an enzyme that degrades dGTP is produced (Wurgler, S. S., and Richardson, C. C. (1990) *Proc. Natl. Acad. Sci. U.S.A.* 87, 2740–2744). Thus, phage T4 strains with variant DNA polymerases with reduced DNA replication activity cannot replicate DNA and produce phage progeny if the nucleotide pools, especially dGTP, are reduced.

In terms of development of a genetic selection strategy, conditions have been established which can be used to identify DNA replication defective DNA polymerases as well as to restrict production of progeny from phages with such defective DNA polymerases, namely the restricted production of phage progeny in infections of the *E. coli* optA1 bacterial host. These conditions, described hereinbelow, enable the selection of further modified (mutated) DNA polymerases with superior DNA replication ability. If the variant DNA polymerases with reduced DNA replication activity are further modified, for example by one or more additional amino acid substitutions, it may be that additional mutations/amino acid substitutions correct or compensate for the initial defect in DNA replication activity. Such further modified DNA polymerases will now be able to replicate DNA in the *E coli* optA1 host and phage progeny will be produced. Thus, detection of phage progeny on the *E. coli* optA1 host in infections with phage formerly restricted from producing progeny on this host allows for the selection of multiply mutant DNA polymerases that have the starting mutation (amino acid substitutions that decrease DNA replication activity) plus one or more new mutations that encode additional amino acid substitutions that correct or compensate for the starting DNA replication defect. The new correcting or compensating mutations (also called suppressor mutations in genetic terminology) can be identified by sequencing the phage DNA polymerase gene using standard procedures (McPheeters, D. S., Christensen, A., Young, E. T., Stormo, G., and Gold, L. (1986) Nucleic Acid Res. 14, 5813–5826; Reha-Krantz, L. J. (1988) J. Mol. Biol. 202, 711–724). The new mutations can be introduced into the phage T4 DNA polymerase gene or into T4 DNA polymerase expression vectors for further study. In contrast to the starting phage T4 DNA polymerases with reduced DNA replication ability, the new variant DNA polymerases have superior DNA replication ability because these variant DNA polymerases were selected on the basis of their ability to overcome, compensate or correct defects in variant DNA polymerase with reduced DNA replication activity. The genetic strategy to identify variant DNA polymerases with superior DNA replication abilities is highly sensitive as a single phage with the above described properties can be selected from a population of $10^8$ to $10^9$ phage.

Further to the invention, variant DNA polymerases with superior DNA replication activity have properties advantageous for DNA sequencing polymerase, such as enhanced primer extension which produces a more uniform distribution of sequencing products and enhanced DNA replication in template regions that may block or hinder replication by unmodified DNA polymerases. T4 DNA polymerase variants with superior DNA replication ability are predicted to improve the quality of DNA sequence information produced by Methods I, II, and III.

The genetic selection strategy described here for the detection of variant DNA polymerases with superior DNA replication ability can be applied to the DNA polymerases of other organisms it such defective DNA polymerases can be identified and if variants with correcting or compensating mutations can be selected.

DNA Sequencing Method I.

T4 DNA polymerase with significantly reduced 3'→5' exonuclease activity, such as variant forms with either D112A+E114A, D219A, or D324A amino acid substitutions, and *E. coli* DNA polymerase II with significantly reduced 3'→5' exonuclease activity, such as the variant form with D156A+E158A amino acid substitutions, can be used as DNA sequencing polymerases with the following set of chain-terminating nucleotides: ddATP, ddGTP, araCTP, and araUTP (FIG. 1).

Figure 2A:
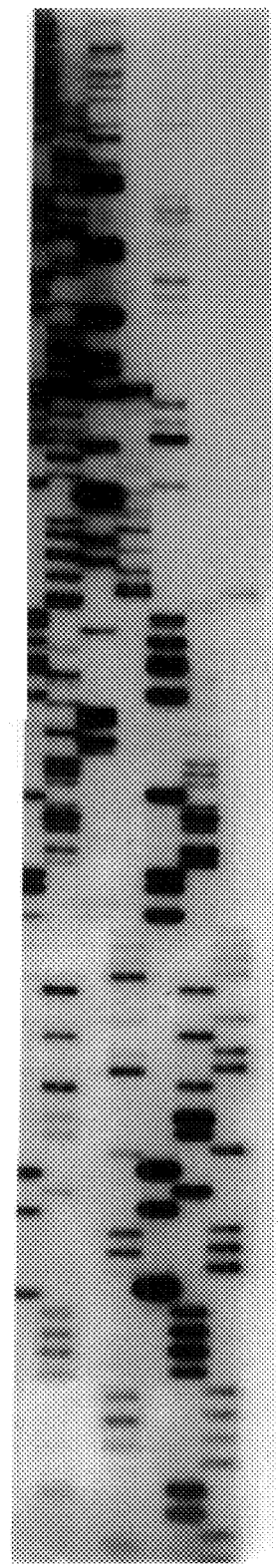
FIGS. 2A–C depict DNA sequencing gels which resulted from the use of variant *E. coli* DNA polymerase II and T4 DNA polymerase.
Figure 2B:
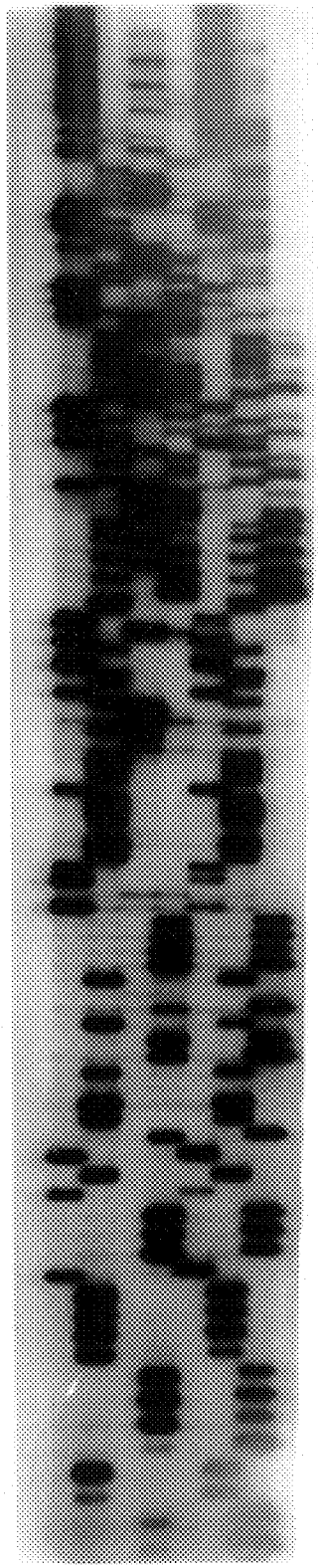
Figure 2C:
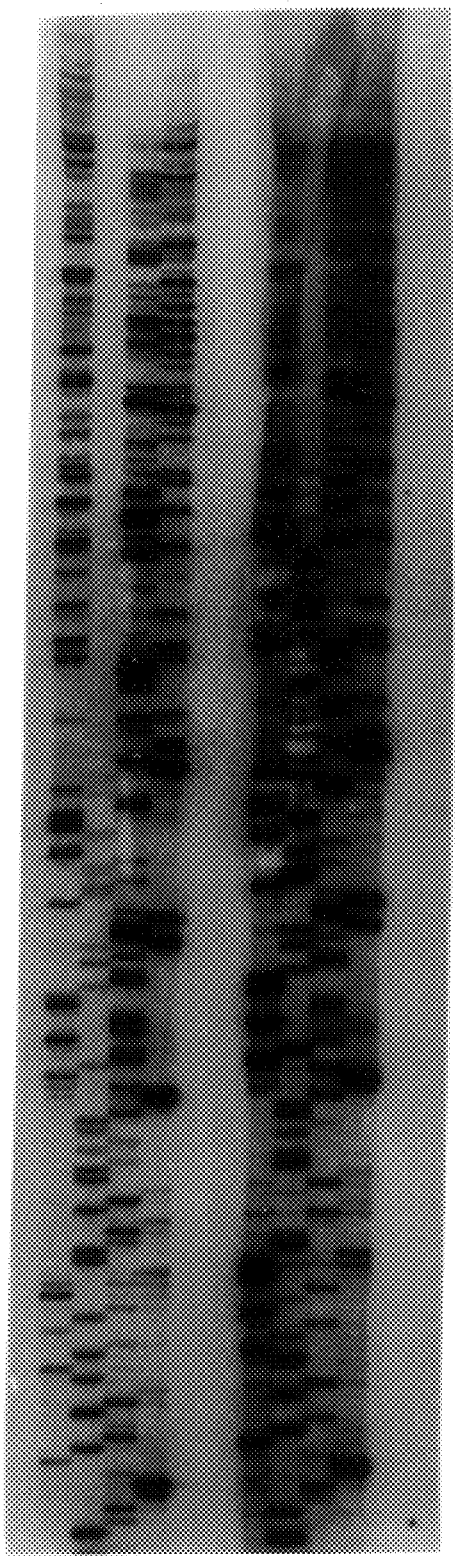

FIG. 2 shows photographs of three DNA sequencing gels. DNA sequencing patterns obtained with Method I are in panels A and B, lanes 1–4, and panel C. Panel A shows DNA sequencing reactions with the exonuclease deficient variant of *E. coli* DNA polymerase II. The reaction with ddGTP is in lane 1, the reaction with ddATP is in lane 2, the reaction with araCTP is in lane 3, and the reaction with araUTP is in lane 4. Panel B shows DNA sequencing reactions with the exonuclease deficient form of bacteriophage T4 DNA polymerase. Again, lane 1 has reactions with ddGTP, lane 2 has ddATP, lane 3 has araCTP, and lane 4 has araUTP. The reactions in panels A and B have $Mg^{2+}$ as the divalent metal cation. Sequencing patters are also obtained with $Mn^{2+}$ in place of $Mg^{2+}$. Method I reactions with $Mn^{2+}$ with the exonuclease deficient form of *E. coli* DNA polymerase II are shown on the left side of panel C, lanes 1–4; reactions with the exonuclease deficient form of T4 DNA polymerase are shown on the right side of panel C, lanes 1–4. Panel C, lanes 1–4 contain reactions with ddGTP (lane 1), ddATP (lane 2), araCTP (lane 3), and araUTP (lane 4).

DNA Sequencing Method II.

Wild type (unmodified) and 3'→5' exonuclease deficient forms of T4 DNA polymerase and the 3'→5' exonuclease deficient form of *E. coli* DNA polymerase II can be used as DNA sequencing polymerases with 3' amino-2', 3'-dideoxyribonucleotides (FIG. 1) as chain terminating nucleotides. Method II reactions for the exonuclease deficient form of *E. coli* DNA polymerase II are shown in FIG. 2, panel A, lanes 5–7. Lane five shows the reaction with 3'amino-2',3'-dideoxyGTP; lane 6 shows the reaction with 3'amino-2',3'-dideoxyATP; lane 7 shows the reaction with 3'amino-2',3-dideoxyTTP. Method II reactions for the exonuclease deficient form of T4 DNA polymerase are shown in panel B, lanes 5–7. Lane 5, 6 and 7 show reactions with 3'amino-2'3'dideoxyGTP, -ATP and -TTP, respectively.

The data demonstrate that the exonuclease deficient forms of *E. coli* DNA polymerase II and bacteriophage T4 DNA polymerases can produce DNA sequence information using a combination of the following chain-terminating nucleotides: ddGTP or 3'amino-2',3'-dideoxyGTP; ddATP or 3'amino-2',3'dideoxyATP; araUTP or 3'amino-2',3'dideoxy-TTP; and araCTP. In view of the good sequence patterns obtained with 3'amino-2'3'dideoxy-GTP, -ATP and -TTP, it is likely that 3'amino-2',3'-dideoxy-CTP will also be an effective chain-terminating nucleotide. No attempt was made to optimize conditions for Methods I or II in order to achieve equal band intensities or to increase the length of readable sequence for the reactions shown in FIG. 2. Nevertheless, the sequencing methods can provide sequence information for at least 300 bases. The exonuclease deficient form of T4 DNA polymerase is not required for sequencing reactions with the 3'amino-2', 3'-dideoxyribonucleoside triphosphates.

Sample Experimental Conditions for Methods I and II (FIG. 2).

Labeling reaction.

5 µl exonuclease deficient DNA polymerase; 300–400 units/ml for T4 DNA polymerase or for E. coli DNA polymerase II. One unit T4 DNA polymerase catalyzes 10 nmol of dTMP incorporation into DNA in 30 min at 30° C. One unit of E. coli DNA polymerase II catalyzes the incorporation of 1 pmol of dTMP into DNA in 1 min at 37° C. Although the reaction is typically conducted at 37° C., the reaction may be conducted in a temperature range from about 35° C. to about 42° C.

15 µl primer-M13 DNA complex, 15 nM

15 µl labeling reaction solution: 2 µM dGTP, dCTP, dTTP; 1 µM [α$^{32}$P]dATP; 50 mM Tris-HCl (pH 8.5); 5 mM MgCl$_2$ or 6 mM MnCl$_2$ for E. coli DNA polymerase II; 5 mM MgCl$_2$ or 0.5 mM MnCl$_2$ for T4 DNA polymerase; 5 mM dithiothreitol; 50 µg/ml bovine serum albumin.

The reaction mixtures were incubated 5 min at 37° C.

The primer may also be labeled at the 5'-end, or by including a labeled nucleotide in the extension reaction and by other standard methods.

Extension Reaction.

4 µl labeling reaction mixture (from above)

4 µl termination solution: 50 µM dGTP, dATP, dCTP and dTTP; and one of the termination analogs listed below:

Method I: ddGTP, 1.6 mM; ddATP, 0.7 mM; araCTP, 0.5 mM; araUTP, 0.5 mM.

Method II: 3'-amino-2',3'-dideoxyGTP, 0.5 mM; 3'-amino-2',3-dideoxyATP, 0.5 mM; 3'-amino-2',3'-dideoxyTTP, 0.5 mM.

Reactions were incubated at 5 min at 37° C. Reactions were stopped by adding formamide/EDTA.

Figure 3:
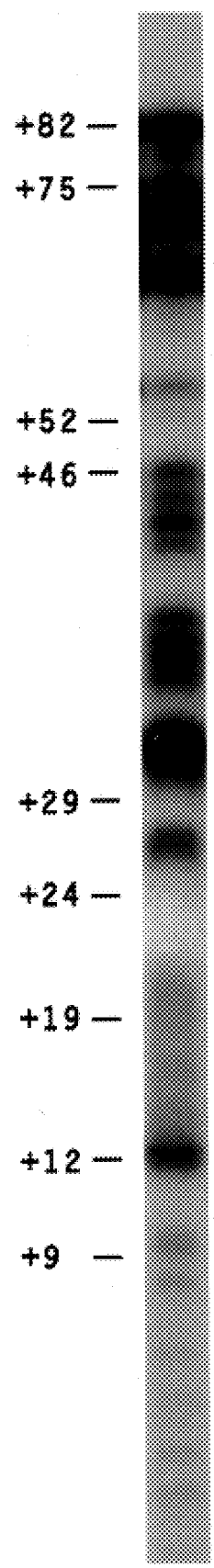
FIG. 3 depicts a DNA sequencing gel in which dATP is used at very low concentrations compared to the other standard nucleotides.

DNA Sequencing Method III (FIG. 3).

Exonuclease deficient T4 DNA polymerase can produce DNA sequence information in reactions where one dNTP is at a low concentration (for example, 0.1 µM to 1 µM) and the other three dNTPs are at high concentrations (100 µM) (FIG. 3). DNA sequencing patterns are produced as with sequencing reactions with nucleotide analogs except that sequencing products produced by this method terminate one position before the dNTP at low concentrations is required.

Sample Experimental Conditions:

25 mM Hepes (pH 7.5)

60 mM NaOAc 1 mM dithiothreitol

100 µM dGTP, dCTP and dTTP 0.1 µM dATP (1 µM dATP for longer DNA products)

0.2 mg/ml bovine serum albumin 7.5 nM 5'[$^{32}$P]labeled primer-template (expressed as the concentration of 3'-primer termini)

30 nM exonuclease deficient T4 DNA polymerase 6 mM Mg(OAc)$_2$

The reaction shown in FIG. 3 contained 0.1 µM dATP and was incubated for 1 min at 30° C. Conditions have not been optimized to obtain high amounts of sequence information; however, reactions in which the low concentration dNTP is at 1 µl yield sequence information greater than 100 bases. Isolation of Novel T4 DNA Polymerases with Properties Advantageous for DNA Sequencing.

The first step in this aspect of the invention is to identify T4 strains with variant (mutant) DNA polymerases defective in some aspect of DNA replication. T4 strains with mutant DNA polymerase that have the amino acid substitutions listed below were chosen, but the genetic selection strategy is not limited to these mutants as any mutant DNA polymerase with defective DNA replication ability can be used. Variant (mutant) T4 DNA polymerases that are partially defective in some aspect of DNA replication cannot replicate DNA in the E. coli optA1 host.

T4 strains with mutant DNA polymerases with amino acid substitutions W213S, I417V, A737V or A777V cannot replicate DNA in the E. coli optA1 host. To achieve these variants the following mutations were employed: for W213S the G nucleotide at position 638 is replaced with a C nucleotide; for I417V the A nucleotide at position 1249 is replaced with a G nucleotide; for A737V the C nucleotide at position 2210 is replaced with a T nucleotide; and for A777V the C nucleotide at position 2330 is replaced with a T nucleotide. As is known other nucleotide replacements can cause the same amino acid changes.

The second step is to select T4 strains that can replicate DNA in the E. coli optA1 host even though the DNA polymerase still retains the amino acid substitution that alone reduces DNA replication ability and prevents replication of DNA in E. coli ontA1 host. T4 strains that have acquired a second DNA polymerase mutation (or multiple mutations), either by spontaneous mutation or by mutagenesis treatment, that encodes a new amino acid substitution that can correct or compensate the DNA replication defect produced by the first amino acid substitution, will be able to replicate DNA in the E. coli optA1 host and produce phage progeny. DNA polymerases thus identified have at least two amino acid substitutions: the starting amino acid substitution and one or more new amino acid substitutions that restore DNA replication activity. This genetic selection strategy is of high sensitivity. A phage with a mutant DNA polymerase containing the starting amino acid substitution and the amino acid substitution(s) that restores DNA replication activity can be selected from a population of 10$^8$ to 10$^9$ phage.

The third step is to identify the DNA replication restoring mutation(s). This step utilizes standard sequencing procedures to find the new mutation(s) in the T4 DNA polymerase gene. Once the new mutation(s) has been identified, the mutation can be introduced into phage or into T4 DNA polymerase expression vectors using standard procedures. Unlike the starting, DNA replication defective DNA polymerase, the DNA polymerases with the correcting or compensating amino acid substitutions have superior DNA replication activity. A sample of the amino acid substitutions discovered using the genetic selection strategy described above include but are not limited to: I50L, G82D, G255S and E743K. To achieve these variants the following mutations were employed: for I50L the A nucleotide at position 148 is replaced with a C nucleotide; for G82D the G nucleotide at position 245 is replaced with an A nucleotide; for G255S the G nucleotide at position 763 is replaced with an A nucleotide; and for E743K the G nucleotide at position 2227 is replaced with an A nucleotide. As is known other nucleotide replacements can effect the same amino acid changes.

Variant (mutant, modified) T4 DNA polymerases with amino acid substitutions that confer enhanced DNA replication activity have new properties advantageous for DNA sequencing. One frequent DNA sequencing problem is that DNA polymerases used in sequencing reactions pause or disassociate at some template sites. As a consequence of this premature stop in chain elongation, sequencing products are produced that are not terminated by a chain-terminating nucleotide. Another problem is that DNA polymerase incorporation of nucleotides and chain-terminating nucleotides is affected by the template sequence which may lead to an unequal distribution of sequencing products. Novel DNA polymerases with enhanced DNA replication activity may surmount these problems. The G82D-T4 DNA polymerase (also known as T4 mel 62 DNA polymerase) has been tested in primer extension assays and this novel DNA polymerase has been found to extend primers that are problematic for the wild type T4 DNA polymerase. An example of G82D-T4 DNA polymerase synthesis is given in FIG. 4.

Figure 4:
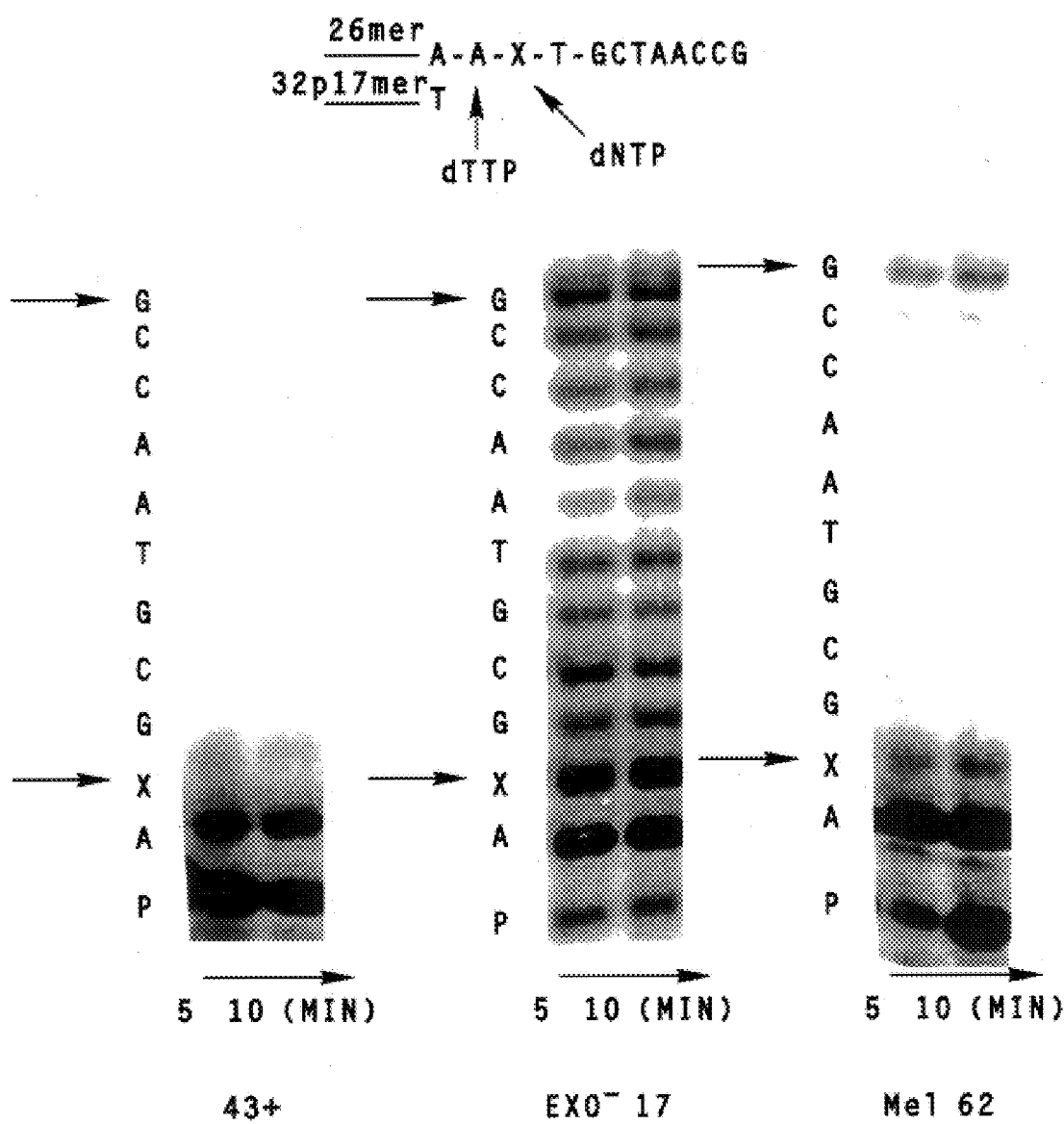
FIG. 4 depicts primer extension past a template abasic site (X) by wild-type and mutant T4 DNA polymerases.

FIG. 4 depicts the use of three T4 polymerases to copy a DNA template lesion (an abasic lesion—a base is missing on the template strand, indicated by X). The wild-type T4 polymerase has difficulty incorporating a nucleotide opposite X, as shown by the very light bands. A 3'-exonuclease deficient T4 polymerase mutant, EXO⁻17, is able to incorporate nucleotides opposite X (note the intense band at X) and continue synthesis beyond the lesion. The T4 mel 62 polymerase is a mutant enzyme (it conveys a mutator phenotype in vivo) that has apparent normal (wild-type) levels of 3'-exonuclease and polymerase activities. It nevertheless is also able to incorporate nucleotides opposite X and to continue synthesis beyond X. What is most interesting is that the absence of "pausing" bands beyond X suggests that the mel 62 DNA polymerase remains bound to the primer template DNA more tightly than either EXO⁻17 or the wild-type polymerases. Thus, it is possible that this enzyme may be able to overcome template and substrate obstacles to synthesize long stretches of DNA.

It is contemplated that one or more amino acid substitutions that confer superior DNA replication activity will be combined with one or more amino acid substitutions that significantly reduce 3'→5' exonuclease activity to create a multiply modified novel T4 DNA polymerase with several properties that are advantageous for DNA sequencing polymerases.

It is known that polymerases, such as bacteriophage T7 DNA polymerase, may be used in conjunction with their accessory proteins thereby increasing the processivity of the polymerase by decreasing the rate of disassociation of the polymerase from the DNA strand to be sequenced.

In the case of the T4 polymerase, its accessory proteins, include but are not limited to, the following T4 gene products: gene product 32, 41, 45 and the 44/62 complex. In the case of *E. coli* DNA polymerase II, the accessory proteins are the following: β protein; the γ protein complex wherein the γ complex is composed of γ, δ, δ', χ, ψ; and SSB (single stranded binding protein) (note that β protein and γ complex are *E. coli* pol III accessory proteins). Use of these accessory proteins enhances the efficiency of the polymerases in sequencing DNA.

While there have been shown and described the fundamental novel features of the invention, it will be understood that various omissions, substitutions and changes in the form and details illustrated may be made by those skilled in the art without departing from the spirit of the invention. It is the invention, therefore, to be limited only as indicated by the scope of the following claims.

We claim:

1. A variant family B DNA polymerase selected from the group consisting of:
   a variant *E coli* DNA polymerase II with the aspartic acid present at its codon position 156 replaced with alanine; and
   a variant *E. coli* DNA polymerase II with the glutamic acid present at its codon position 158 is replaced with alanine.

2. A variant family B DNA polymerase, said variant polymerase selected from the group consisting of T2, T4, and T6 DNA polymerases, characterized in that the aspartic acid present at its codon position 112 is replaced with alanine and the glutamic acid present at its codon position 114 is replaced with alanine.

3. The variant *E. coli* DNA polymerase II of claim 1, characterized in that the aspartic acid at its codon position 156 is replaced with alanine and the glutamic acid present at its codon position 158 is replaced with alanine.

4. A variant family B DNA polymerase for use in DNA sequencing, said variant polymerase selected from the group consisting of T2, T4, and T6 DNA polymerases, said variant polymerase comprising at least one mutation, wherein the mutation reduces 3'→5' exonuclease activity and is selected from the group consisting of:
   aspartic acid replaced with alanine at codon position 112;
   glutamic acid replaced with alanine at codon position 114;
   aspartic acid replaced with alanine at codon position 219; and
   aspartic replaced with alanine at codon position 324.

5. A variant family B DNA polymerase for use in DNA sequencing, said variant polymerase selected from the group consisting of T2, T4, and T6 DNA polymerases, said variant polymerase comprising at least two mutations, wherein:
   1) a first mutation reduces 3'→5' exonuclease activity and is selected from the group consisting of:
      a) aspartic acid replaced with alanine at codon position 112,
      b) glutamic acid replaced with alanine at codon position 114,
      c) aspartic acid replaced with alanine at codon position 219,
      d) glycine replaced with serine at codon position 255, and
      e) aspartic acid replaced with alanine at codon position 324; and
   2) a second mutation is selected from the group consisting of:
      a) isoleucine replaced with leucine at codon position 50,
      b) glycine replaced with aspartic acid at codon position 82, and
      c) glutamic acid replaced with lysine at codon position 743.

6. A variant family B DNA polymerase for use in DNA sequencing, said variant polymerase selected from the group consisting of T2, T4, and T6 DNA polymerases, the variant polymerase comprising at least one mutation, the mutation selected from the group consisting of:
   isoleucine replaced with leucine at codon position 50; and
   glutamic acid replaced with lysine at codon position 743.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 2694 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1..2694

(xi) SEQUENCE DESCRIPTION: SEQ ID NO:1:

```
ATG AAA GAA TTT TAT ATC TCT ATC GAA ACA GTC GGA AAT AAT ATT      45
Met Lys Glu Phe Tyr Ile Ser Ile Glu Thr Val Gly Asn Asn Ile
              5                  10                  15

ATT GAA CGT TAT ATT GAT GAA AAC GGA AAG GAA CGT ACT CGT GAA      90
Ile Glu Arg Tyr Ile Asp Glu Asn Gly Lys Glu Arg Thr Arg Glu
             20                  25                  30

GTA GAA TAT CTT CCG ACT ATG TTT AGG CAT TGT AAG GAA GAG TCA     135
Val Glu Tyr Leu Pro Thr Met Phe Arg His Cys Lys Glu Glu Ser
```

-continued

|  | 35 |  |  |  | 40 |  |  |  | 45 |  |  |  |
|---|---|---|---|---|---|---|---|---|---|---|---|---|
| AAA | TAC | AAA | GAC | ATC | TAT | GGT | AAA | AAC | TGT | GCT | CCT | CAA | AAA | TTT | 180 |
| Lys | Tyr | Lys | Asp | Ile | Tyr | Gly | Lys | Asn | Cys | Ala | Pro | Gln | Lys | Phe |  |
|  |  |  | 50 |  |  |  |  | 55 |  |  |  |  | 60 |  |  |

```
AAA TAC AAA GAC ATC TAT GGT AAA AAC TGT GCT CCT CAA AAA TTT      180
Lys Tyr Lys Asp Ile Tyr Gly Lys Asn Cys Ala Pro Gln Lys Phe
            50                  55                  60

CCA TCA ATG AAA GAT GCT CGA GAT TGG ATG AAG CGA ATG GAA GAC      225
Pro Ser Met Lys Asp Ala Arg Asp Trp Met Lys Arg Met Glu Asp
            65                  70                  75

ATC GGT CTC GAA GCT CTC GGT ATG AAC GAT TTT AAA CTC GCT TAT      270
Ile Gly Leu Glu Ala Leu Gly Met Asn Asp Phe Lys Leu Ala Tyr
            80                  85                  90

ATC AGT GAT ACG TAT GGT TCA GAA ATT GTT TAT GAC CGA AAA TTT      315
Ile Ser Asp Thr Tyr Gly Ser Glu Ile Val Tyr Asp Arg Lys Phe
            95                  100                 105

GTT CGT GTA GCT AAC TGT GAC ATT GAG GTT ACT GGT GAT AAA TTT      360
Val Arg Val Ala Asn Cys Asp Ile Glu Val Thr Gly Asp Lys Phe
            110                 115                 120

CCT GAC CCA ATG AAA GCA GAA TAT GAA ATT GAT GCT ATC ACT CAT      405
Pro Asp Pro Met Lys Ala Glu Tyr Glu Ile Asp Ala Ile Thr His
            125                 130                 135

TAT GAT TCA ATT GAC GAC CGT TTT TAT GTT TTC GAC CTT TTG AAT      450
Tyr Asp Ser Ile Asp Asp Arg Phe Tyr Val Phe Asp Leu Leu Asn
            140                 145                 150

TCA ATG TAC GGT TCA GTA TCA AAA TGG GAT GCA AAG TTA GCT GCT      495
Ser Met Tyr Gly Ser Val Ser Lys Trp Asp Ala Lys Leu Ala Ala
            155                 160                 165

AAG CTT GAC TGT GAA GGT GGT GAT GAA GTT CCT CAA GAA ATT CTT      540
Lys Leu Asp Cys Glu Gly Gly Asp Glu Val Pro Gln Glu Ile Leu
            170                 175                 180

GAC CGA GTA ATT TAT ATG CCA TTT GAT AAT GAG CGT GAT ATG CTC      585
Asp Arg Val Ile Tyr Met Pro Phe Asp Asn Glu Arg Asp Met Leu
            185                 190                 195

ATG GAA TAT ATT AAT CTC TGG GAA CAG AAA CGA CCT GCT ATT TTT      630
Met Glu Tyr Ile Asn Leu Trp Glu Gln Lys Arg Pro Ala Ile Phe
            200                 205                 210

ACT GGT TGG AAT ATT GAG GGG TTT GAC GTT CCG TAT ATC ATG AAT      675
Thr Gly Trp Asn Ile Glu Gly Phe Asp Val Pro Tyr Ile Met Asn
            215                 220                 225

CGC GTT AAA ATG ATT CTG GGT GAA CGC AGT ATG AAA CGT TTC TCT      720
Arg Val Lys Met Ile Leu Gly Glu Arg Ser Met Lys Arg Phe Ser
            230                 235                 240

CCA ATC GGT CGG GTA AAA TCT AAA CTA ATT CAA AAT ATG TAC GGT      765
Pro Ile Gly Arg Val Lys Ser Lys Leu Ile Gln Asn Met Tyr Gly
            245                 250                 255

AGC AAA GAA ATT TAT TCT ATT GAT GGC GTA TCT ATT CTT GAT TAT      810
Ser Lys Glu Ile Tyr Ser Ile Asp Gly Val Ser Ile Leu Asp Tyr
            260                 265                 270

TTA GAT TTG TAC AAG AAA TTC GCT TTT ACT AAT TTG CCG TCA TTC      855
Leu Asp Leu Tyr Lys Lys Phe Ala Phe Thr Asn Leu Pro Ser Phe
            275                 280                 285

TCT TTG GAA TCA GTT GCT CAA CAT GAA ACC AAA AAA GGT AAA TTA      900
Ser Leu Glu Ser Val Ala Gln His Glu Thr Lys Lys Gly Lys Leu
            290                 295                 300

CCA TAC GAC GGT CCT ATT AAT AAA CTT CGT GAG ACT AAT CAT CAA      945
Pro Tyr Asp Gly Pro Ile Asn Lys Leu Arg Glu Thr Asn His Gln
            305                 310                 315

CGA TAC ATT AGT TAT AAC ATC ATT GAC GTA GAA TCA GTT CAA GCA      990
Arg Tyr Ile Ser Tyr Asn Ile Ile Asp Val Glu Ser Val Gln Ala
            320                 325                 330

ATT GAT AAA ATT CGT GGG TTT ATC GAT CTA GTT TTA AGT ATG TCT     1035
Ile Asp Lys Ile Arg Gly Phe Ile Asp Leu Val Leu Ser Met Ser
```

-continued

```
                      335                  340                     345
TAT TAT GCT AAA ATG CCT TTT TCT GGT GTA ATG AGT CCT ATT AAA  1080
Tyr Tyr Ala Lys Met Pro Phe Ser Gly Val Met Ser Pro Ile Lys
                      350                 355                  360

ACT TGG GAT GCT ATT ATT TTT AAC TCA TTG AAA GGT GAA CAC AAG  1125
Thr Trp Asp Ala Ile Ile Phe Asn Ser Leu Lys Gly Glu His Lys
                      365                 370                  375

GTT ATT CCT CAA CAA GGT TCG CAC GTT AAA CAG AGT TTT CCG GGT  1170
Val Ile Pro Gln Gln Gly Ser His Val Lys Gln Ser Phe Pro Gly
                      380                 385                  390

GCA TTT GTA TTT GAA CCT AAA CCA ATT GCT CGT CGA TAC ATT ATG  1215
Ala Phe Val Phe Glu Pro Lys Pro Ile Ala Arg Arg Tyr Ile Met
                      395                 400                  405

AGT TTT GAC TTG ACG TCT CTG TAT CCG AGC ATT ATT CGC CAG GTT  1260
Ser Phe Asp Leu Thr Ser Leu Tyr Pro Ser Ile Ile Arg Gln Val
                      410                 415                  420

AAC ATT AGT CCT GAA ACT ATT CGT GGT CAG TTT AAA GTT CAT CCA  1305
Asn Ile Ser Pro Glu Thr Ile Arg Gly Gln Phe Lys Val His Pro
                      425                 430                  435

ATT CAT GAA TAT ATC GCA GGA ACA GCT CCT AAA CCA AGT GAT GAA  1350
Ile His Glu Tyr Ile Ala Gly Thr Ala Pro Lys Pro Ser Asp Glu
                      440                 445                  450

TAT TCT TGT TCT CCG AAT GGA TGG ATG TAT GAT AAG CAT CAA GAA  1395
Tyr Ser Cys Ser Pro Asn Gly Trp Met Tyr Asp Lys His Gln Glu
                      455                 460                  465

GGT ATC ATT CCA AAG GAA ATC GCT AAA GTA TTT TTC CAG CGT AAA  1440
Gly Ile Ile Pro Lys Glu Ile Ala Lys Val Phe Phe Gln Arg Lys
                      470                 475                  480

GAT TGG AAA AAG AAA ATG TTC GCT GAA GAA ATG AAT GCC GAA GCT  1485
Asp Trp Lys Lys Lys Met Phe Ala Glu Glu Met Asn Ala Glu Ala
                      485                 490                  495

ATT AAA AAG ATT ATT ATG AAA GGC GCA GGG TCT TGT TCA ACT AAA  1530
Ile Lys Lys Ile Ile Met Lys Gly Ala Gly Ser Cys Ser Thr Lys
                      500                 505                  510

CCA GAA GTT GAA CGA TAT GTT AAG TTC ACT GAT GAT TTC TTA AAT  1575
Pro Glu Val Glu Arg Tyr Val Lys Phe Thr Asp Asp Phe Leu Asn
                      515                 520                  525

GAA CTA TCG AAT TAT ACT GAA TCT GTT CTT AAT AGT CTG ATT GAA  1620
Glu Leu Ser Asn Tyr Thr Glu Ser Val Leu Asn Ser Leu Ile Glu
                      530                 535                  540

GAA TGT GAA AAA GCA GCT ACA CTT GCT AAT ACA AAT CAG CTG AAC  1665
Glu Cys Glu Lys Ala Ala Thr Leu Ala Asn Thr Asn Gln Leu Asn
                      545                 550                  555

CGT AAA ATT CTT ATT AAC AGT CTT TAT GGT GCT CTT GGT AAT ATT  1710
Arg Lys Ile Leu Ile Asn Ser Leu Tyr Gly Ala Leu Gly Asn Ile
                      560                 565                  570

CAT TTC CGT TAC TAT GAT TTA CGA AAT GCT ACT GCT ATC ACA ATT  1755
His Phe Arg Tyr Tyr Asp Leu Arg Asn Ala Thr Ala Ile Thr Ile
                      575                 580                  585

TTT GGT CAA GTT GGT ATT CAG TGG ATT GCT CGT AAA ATT AAT GAA  1800
Phe Gly Gln Val Gly Ile Gln Trp Ile Ala Arg Lys Ile Asn Glu
                      590                 595                  600

TAT CTG AAT AAA GTA TGC GGA ACT AAT GAT GAA GAT TTC ATC GCA  1845
Tyr Leu Asn Lys Val Cys Gly Thr Asn Asp Glu Asp Phe Ile Ala
                      605                 610                  615

GCA GGT GAT ACT GAT TCG GTA TAT GTT TGT GTA GAT AAA GTT ATT  1890
Ala Gly Asp Thr Asp Ser Val Tyr Val Cys Val Asp Lys Val Ile
                      620                 625                  630

GAA AAA GTT GGT CTT GAC CGA TTC AAA GAG CAG AAC GAT TTG GTT  1935
Glu Lys Val Gly Leu Asp Arg Phe Lys Glu Gln Asn Asp Leu Val
```

-continued

```
                635                 640                 645
GAA TTC ATG AAT CAG TTT GGT AAG AAA AAG ATG GAA CCT ATG ATT      1980
Glu Phe Met Asn Gln Phe Gly Lys Lys Lys Met Glu Pro Met Ile
                650                 655                 660

GAT GTT GCA TAT CGT GAG TTA TGT GAT TAT ATG AAT AAC CGC GAG      2025
Asp Val Ala Tyr Arg Glu Leu Cys Asp Tyr Met Asn Asn Arg Glu
                665                 670                 675

CAT CTG ATG CAT ATG GAC CGT GAA GCT ATT TCT TGC CCT CCG CTT      2070
His Leu Met His Met Asp Arg Glu Ala Ile Ser Cys Pro Pro Leu
                680                 685                 690

GGT TCA AAG GGT GTT GGT GGA TTT TGG AAA GCG AAA AAA CGT TAT      2115
Gly Ser Lys Gly Val Gly Gly Phe Trp Lys Ala Lys Lys Arg Tyr
                695                 700                 705

GCT CTG AAC GTT TAT GAT ATG GAA GAT AAG CGA TTT GCT GAA CCG      2160
Ala Leu Asn Val Tyr Asp Met Glu Asp Lys Arg Phe Ala Glu Pro
                710                 715                 720

CAT CTA AAA ATC ATG GGT ATG GAA ACT CAG CAG AGT TCA ACA CCA      2205
His Leu Lys Ile Met Gly Met Glu Thr Gln Gln Ser Ser Thr Pro
                725                 730                 735

AAA GCA GTG CAA GAA GCA CTC GAA GAA AGT ATT CGT CGT ATT CTT      2250
Lys Ala Val Gln Glu Ala Leu Glu Glu Ser Ile Arg Arg Ile Leu
                740                 745                 750

CAG GAA GGC GAA GAG TCT GTC CAA GAA TAT TAC AAG AAC TTC GAG      2295
Gln Glu Gly Glu Glu Ser Val Gln Glu Tyr Tyr Lys Asn Phe Glu
                755                 760                 765

AAA GAA TAT CGT CAA CTT GAC TAT AAA GTT ATT GCT GAA GTA AAA      2340
Lys Glu Tyr Arg Gln Leu Asp Tyr Lys Val Ile Ala Glu Val Lys
                770                 775                 780

ACT GCG AAC GAT ATA GCG AAA TAT GAT GAT AAA GGT TGG CCA GGA      2385
Thr Ala Asn Asp Ile Ala Lys Tyr Asp Asp Lys Gly Trp Pro Gly
                795                 790                 795

TTT AAA TGT CCG TTC CAT ATT CGT GGT GTG CTA ACT TAT CGT CGA      2430
Phe Lys Cys Pro Phe His Ile Arg Gly Val Leu Thr Tyr Arg Arg
                800                 805                 810

GCT GTT AGT GGT CTG GGT GTA GCT CCA ATT TTG GAT GGA AAT AAA      2475
Ala Val Ser Gly Leu Gly Val Ala Pro Ile Leu Asp Gly Asn Lys
                815                 820                 825

GTA ATG GTT CTT CCA TTA CGT GAA GGA AAT CCG TTT GGT GAT AAG      2520
Val Met Val Leu Pro Leu Arg Glu Gly Asn Pro Phe Gly Asp Lys
                830                 835                 840

TGC ATT GCT TGG CCA TCG GGT ACA GAA CTT CCA AAA GAA ATT CGT      2565
Cys Ile Ala Trp Pro Ser Gly Thr Glu Leu Pro Lys Glu Ile Arg
                845                 850                 855

TCT GAT GTA CTA TCT TGG ATT GAC TAC TCA ACT TTG TTC CAA AAA      2610
Ser Asp Val Leu Ser Trp Ile Asp Tyr Ser Thr Leu Phe Gln Lys
                860                 865                 870

TCG TTT GTT AAA CCG CTT GCG GGT ATG TGT GAA TCG GCA GGT ATG      2655
Ser Phe Val Lys Pro Leu Ala Gly Met Cys Glu Ser Ala Gly Met
                875                 880                 885

GAC TAT GAG GAA AAA GCT TCG TTA GAC TTC CTG TTT GGC              2694
Asp Tyr Glu Glu Lys Ala Ser Leu Asp Phe Leu Phe Gly
                890                 895     898
```

(2) INFORMATION FOR SEQ ID NO:2:

(i) SEQUENCE CHARACTERISTICS:
        (A) LENGTH: 898 amino acids
        (B) TYPE: amino acid
        (D) TOPOLOGY: linear (ii) MOLECULE TYPE: protein (xi) SEQUENCE DESCRIPTION: SEQ ID NO:2:

```
Met Lys Glu Phe Tyr Ile Ser Ile Glu Thr Val Gly Asn Asn Ile
              5                  10                  15

Ile Glu Arg Tyr Ile Asp Glu Asn Gly Lys Glu Arg Thr Arg Glu
             20                  25                  30

Val Glu Tyr Leu Pro Thr Met Phe Arg His Cys Lys Glu Glu Ser
             35                  40                  45

Lys Tyr Lys Asp Ile Tyr Gly Lys Asn Cys Ala Pro Gln Lys Phe
             50                  55                  60

Pro Ser Met Lys Asp Ala Arg Asp Trp Met Lys Arg Met Glu Asp
             65                  70                  75

Ile Gly Leu Glu Ala Leu Gly Met Asn Asp Phe Lys Leu Ala Tyr
             80                  85                  90

Ile Ser Asp Thr Tyr Gly Ser Glu Ile Val Tyr Asp Arg Lys Phe
             95                 100                 105

Val Arg Val Ala Asn Cys Asp Ile Glu Val Thr Gly Asp Lys Phe
            110                 115                 120

Pro Asp Pro Met Lys Ala Glu Tyr Glu Ile Asp Ala Ile Thr His
            125                 130                 135

Tyr Asp Ser Ile Asp Asp Arg Phe Tyr Val Phe Asp Leu Leu Asn
            140                 145                 150

Ser Met Tyr Gly Ser Val Ser Lys Trp Asp Ala Lys Leu Ala Ala
            155                 160                 165

Lys Leu Asp Cys Glu Gly Gly Asp Glu Val Pro Gln Glu Ile Leu
            170                 175                 180

Asp Arg Val Ile Tyr Met Pro Phe Asp Asn Glu Arg Asp Met Leu
            185                 190                 195

Met Glu Tyr Ile Asn Leu Trp Glu Gln Lys Arg Pro Ala Ile Phe
            200                 205                 210

Thr Gly Trp Asn Ile Glu Gly Phe Asp Val Pro Tyr Ile Met Asn
            215                 220                 225

Arg Val Lys Met Ile Leu Gly Glu Arg Ser Met Lys Arg Phe Ser
            230                 235                 240

Pro Ile Gly Arg Val Lys Ser Lys Leu Ile Gln Asn Met Tyr Gly
            245                 250                 255

Ser Lys Glu Ile Tyr Ser Ile Asp Gly Val Ser Ile Leu Asp Tyr
            260                 265                 270

Leu Asp Leu Tyr Lys Lys Phe Ala Phe Thr Asn Leu Pro Ser Phe
            275                 280                 285

Ser Leu Glu Ser Val Ala Gln His Glu Thr Lys Lys Gly Lys Leu
            290                 295                 300

Pro Tyr Asp Gly Pro Ile Asn Lys Leu Arg Glu Thr Asn His Gln
            305                 310                 315

Arg Tyr Ile Ser Tyr Asn Ile Ile Asp Val Glu Ser Val Gln Ala
            320                 325                 330

Ile Asp Lys Ile Arg Gly Phe Ile Asp Leu Val Leu Ser Met Ser
            335                 340                 345

Tyr Tyr Ala Lys Met Pro Phe Ser Gly Val Met Ser Pro Ile Lys
            350                 355                 360

Thr Trp Asp Ala Ile Ile Phe Asn Ser Leu Lys Gly Glu His Lys
            365                 370                 375

Val Ile Pro Gln Gln Gly Ser His Val Lys Gln Ser Phe Pro Gly
            380                 385                 390
```

```
Ala Phe Val Phe Glu Pro Lys Pro Ile Ala Arg Arg Tyr Ile Met
            395                 400                 405

Ser Phe Asp Leu Thr Ser Leu Tyr Pro Ser Ile Ile Arg Gln Val
            410                 415                 420

Asn Ile Ser Pro Glu Thr Ile Arg Gly Gln Phe Lys Val His Pro
            425                 430                 435

Ile His Glu Tyr Ile Ala Gly Thr Ala Pro Lys Pro Ser Asp Glu
            440                 445                 450

Tyr Ser Cys Ser Pro Asn Gly Trp Met Tyr Asp Lys His Gln Glu
            455                 460                 465

Gly Ile Ile Pro Lys Glu Ile Ala Lys Val Phe Phe Gln Arg Lys
            470                 475                 480

Asp Trp Lys Lys Lys Met Phe Ala Glu Glu Met Asn Ala Glu Ala
            485                 490                 495

Ile Lys Lys Ile Ile Met Lys Gly Ala Gly Ser Cys Ser Thr Lys
            500                 505                 510

Pro Glu Val Glu Arg Tyr Val Lys Phe Thr Asp Asp Phe Leu Asn
            515                 520                 525

Glu Leu Ser Asn Tyr Thr Glu Ser Val Leu Asn Ser Leu Ile Glu
            530                 535                 540

Glu Cys Glu Lys Ala Ala Thr Leu Ala Asn Thr Asn Gln Leu Asn
            545                 550                 555

Arg Lys Ile Leu Ile Asn Ser Leu Tyr Gly Ala Leu Gly Asn Ile
            560                 565                 570

His Phe Arg Tyr Tyr Asp Leu Arg Asn Ala Thr Ala Ile Thr Ile
            575                 580                 585

Phe Gly Gln Val Gly Ile Gln Trp Ile Ala Arg Lys Ile Asn Glu
            590                 595                 600

Tyr Leu Asn Lys Val Cys Gly Thr Asn Asp Glu Asp Phe Ile Ala
            605                 610                 615

Ala Gly Asp Thr Asp Ser Val Tyr Val Cys Val Asp Lys Val Ile
            620                 625                 630

Glu Lys Val Gly Leu Asp Arg Phe Lys Glu Gln Asn Asp Leu Val
            635                 640                 645

Glu Phe Met Asn Gln Phe Gly Lys Lys Lys Met Glu Pro Met Ile
            650                 655                 660

Asp Val Ala Tyr Arg Glu Leu Cys Asp Tyr Met Asn Asn Arg Glu
            665                 670                 675

His Leu Met His Met Asp Arg Glu Ala Ile Ser Cys Pro Pro Leu
            680                 685                 690

Gly Ser Lys Gly Val Gly Gly Phe Trp Lys Ala Lys Lys Arg Tyr
            695                 700                 705

Ala Leu Asn Val Tyr Asp Met Glu Asp Lys Arg Phe Ala Glu Pro
            710                 715                 720

His Leu Lys Ile Met Gly Met Glu Thr Gln Gln Ser Ser Thr Pro
            725                 730                 735

Lys Ala Val Gln Glu Ala Leu Glu Glu Ser Ile Arg Arg Ile Leu
            740                 745                 750

Gln Glu Gly Glu Glu Ser Val Gln Glu Tyr Tyr Lys Asn Phe Glu
            755                 760                 765

Lys Glu Tyr Arg Gln Leu Asp Tyr Lys Val Ile Ala Glu Val Lys
            770                 775                 780

Thr Ala Asn Asp Ile Ala Lys Tyr Asp Asp Lys Gly Trp Pro Gly
            785                 790                 795
```

```
Phe Lys Cys Pro Phe His Ile Arg Gly Val Leu Thr Tyr Arg Arg
                800                 805                 810

Ala Val Ser Gly Leu Gly Val Ala Pro Ile Leu Asp Gly Asn Lys
                815                 820                 825

Val Met Val Leu Pro Leu Arg Glu Gly Asn Pro Phe Gly Asp Lys
                830                 835                 840

Cys Ile Ala Trp Pro Ser Gly Thr Glu Leu Pro Lys Glu Ile Arg
                845                 850                 855

Ser Asp Val Leu Ser Trp Ile Asp Tyr Ser Thr Leu Phe Gln Lys
                860                 865                 870

Ser Phe Val Lys Pro Leu Ala Gly Met Cys Glu Ser Ala Gly Met
                875                 880                 885

Asp Tyr Glu Glu Lys Ala Ser Leu Asp Phe Leu Phe Gly
                890                 895             898
```

(2) INFORMATION FOR SEQ ID NO:3:

(i) SEQUENCE CHARACTERISTICS:
        (A) LENGTH: 2694 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..2694

(xi) SEQUENCE DESCRIPTION: SEQ ID NO:3:

```
ATG AAA GAA TTT TAT ATC TCT ATT GAA ACA GTC GGA AAT AAC ATT      45
Met Lys Glu Phe Tyr Ile Ser Ile Glu Thr Val Gly Asn Asn Ile
              5                  10                  15

GTT GAA CGT TAT ATT GAT GAA AAT GGA AAG GAA CGT ACC CGT GAA      90
Val Glu Arg Tyr Ile Asp Glu Asn Gly Lys Glu Arg Thr Arg Glu
             20                  25                  30

GTA GAA TAT CTT CCA ACT ATG TTT AGG CAT TGT AAG GAA GAG TCA     135
Val Glu Tyr Leu Pro Thr Met Phe Arg His Cys Lys Glu Glu Ser
             35                  40                  45

AAA TAC AAA GAC ATC TAT GGT AAA AAC TGC GCT CCT CAA AAA TTT     180
Lys Tyr Lys Asp Ile Tyr Gly Lys Asn Cys Ala Pro Gln Lys Phe
             50                  55                  60

CCA TCA ATG AAA GAT GCT CGA GAT TGG ATG AAG CGA ATG GAA GAC     225
Pro Ser Met Lys Asp Ala Arg Asp Trp Met Lys Arg Met Glu Asp
             65                  70                  75

ATC GGT CTC GAA GCT CTC GGT ATG AAC GAT TTT AAA CTC GCT TAT     270
Ile Gly Leu Glu Ala Leu Gly Met Asn Asp Phe Lys Leu Ala Tyr
             80                  85                  90

ATA AGT GAT ACA TAT GGT TCA GAA ATT GTT TAT GAC CGA AAA TTT     315
Ile Ser Asp Thr Tyr Gly Ser Glu Ile Val Tyr Asp Arg Lys Phe
             95                 100                 105

GTT CGT GTA GCT AAC TGT GAC ATT GAG GTT ACT GGT GAT AAA TTT     360
Val Arg Val Ala Asn Cys Asp Ile Glu Val Thr Gly Asp Lys Phe
            110                 115                 120

CCT GAC CCA ATG AAA GCA GAA TAT GAA ATT GAT GCT ATC ACT CAT     405
Pro Asp Pro Met Lys Ala Glu Tyr Glu Ile Asp Ala Ile Thr His
            125                 130                 135

TAC GAT TCA ATT GAC GAT CGT TTT TAT GTT TTC GAC CTT TTG AAT     450
Tyr Asp Ser Ile Asp Asp Arg Phe Tyr Val Phe Asp Leu Leu Asn
            140                 145                 150

TCA ATG TAC GGT TCA GTA TCA AAA TGG GAT GCA AAG TTA GCT GCT     495
```

```
            Ser Met Tyr Gly Ser Val Ser Lys Trp Asp Ala Lys Leu Ala Ala
                            155                 160                 165

AAG CTT GAC TGT GAA GGT GGT GAT GAA GTT CCT CAA GAA ATT CTT         540
Lys Leu Asp Cys Glu Gly Gly Asp Glu Val Pro Gln Glu Ile Leu
                170                 175                 180

GAC CGA GTA ATT TAT ATG CCA TTC GAT AAT GAG CGT GAT ATG CTC         585
Asp Arg Val Ile Tyr Met Pro Phe Asp Asn Glu Arg Asp Met Leu
                    185                 190                 195

ATG GAA TAT ATC AAT CTT TGG GAA CAG AAA CGA CCT GCT ATT TTT         630
Met Glu Tyr Ile Asn Leu Trp Glu Gln Lys Arg Pro Ala Ile Phe
                    200                 205                 210

ACT GGT TGG AAT ATT GAG GGG TTT GAC GTT CCG TAT ATC ATG AAT         675
Thr Gly Trp Asn Ile Glu Gly Phe Asp Val Pro Tyr Ile Met Asn
                    215                 220                 225

CGT GTT AAA ATG ATT CTG GGT GAA CGT AGT ATG AAA CGT TTC TCT         720
Arg Val Lys Met Ile Leu Gly Glu Arg Ser Met Lys Arg Phe Ser
                    230                 235                 240

CCA ATC GGT CGG GTA AAA TCT AAA CTA ATT CAA AAT ATG TAC GGT         765
Pro Ile Gly Arg Val Lys Ser Lys Leu Ile Gln Asn Met Tyr Gly
                    245                 250                 255

AGC AAA GAA ATT TAT TCT ATT GAT GGC GTA TCT ATT CTT GAT TAT         810
Ser Lys Glu Ile Tyr Ser Ile Asp Gly Val Ser Ile Leu Asp Tyr
                    260                 265                 270

TTA GAT TTG TAC AAG AAA TTC GCT TTT ACT AAT TTG CCG TCA TTC         855
Leu Asp Leu Tyr Lys Lys Phe Ala Phe Thr Asn Leu Pro Ser Phe
                    275                 280                 285

TCT TTG GAA TCA GTT GCT CAA CAT GAA ACC AAA AAA GGT AAA TTA         900
Ser Leu Glu Ser Val Ala Gln His Glu Thr Lys Lys Gly Lys Leu
                    290                 295                 300

CCA TAC GAC GGT CCT ATT AAT AAA CTT CGT GAG ACT AAT CAT CAA         945
Pro Tyr Asp Gly Pro Ile Asn Lys Leu Arg Glu Thr Asn His Gln
                    305                 310                 315

CGA TAC ATT AGT TAT AAC ATC ATT GAC GTA GAA TCA GTT CAA GCA         990
Arg Tyr Ile Ser Tyr Asn Ile Ile Asp Val Glu Ser Val Gln Ala
                    320                 325                 330

ATC GAT AAA ATT CGT GGG TTT ATC GAT CTA GTT TTA AGT ATG TCT        1035
Ile Asp Lys Ile Arg Gly Phe Ile Asp Leu Val Leu Ser Met Ser
                    335                 340                 345

TAT TAC GCT AAA ATG CCT TTT TCT GGT GTA ATG AGT CCT ATT AAA        1080
Tyr Tyr Ala Lys Met Pro Phe Ser Gly Val Met Ser Pro Ile Lys
                    350                 355                 360

ACT TGG GAT GCT ATT ATT TTT AAC TCA TTG AAA GGT GAA CAT AAG        1125
Thr Trp Asp Ala Ile Ile Phe Asn Ser Leu Lys Gly Glu His Lys
                    365                 370                 375

GTT ATT CCT CAA CAA GGT TCG CAC GTT AAA CAG AGT TTT CCG GGT        1170
Val Ile Pro Gln Gln Gly Ser His Val Lys Gln Ser Phe Pro Gly
                    380                 385                 390

GCA TTT GTG TTT GAA CCT AAA CCA ATT GCA CGT CGA TAC ATT ATG        1215
Ala Phe Val Phe Glu Pro Lys Pro Ile Ala Arg Arg Tyr Ile Met
                    395                 400                 405

AGT TTT GAC TTG ACG TCT CTG TAT CCG AGC ATT ATT CGC CAG GTT        1260
Ser Phe Asp Leu Thr Ser Leu Tyr Pro Ser Ile Ile Arg Gln Val
                    410                 415                 420

AAC ATT AGT CCT GAA ACT ATT CGT GGT CAG TTT AAA GTT CAT CCA        1305
Asn Ile Ser Pro Glu Thr Ile Arg Gly Gln Phe Lys Val His Pro
                    425                 430                 435

ATT CAT GAA TAT ATC GCA GGA ACA GCT CCT AAA CCG AGT GAT GAA        1350
Ile His Glu Tyr Ile Ala Gly Thr Ala Pro Lys Pro Ser Asp Glu
                    440                 445                 450

TAT TCT TGT TCT CCG AAT GGA TGG ATG TAT GAT AAA CAT CAA GAA        1395
```

-continued

```
                Tyr Ser Cys Ser Pro Asn Gly Trp Met Tyr Asp Lys His Gln Glu
                                455                 460                 465

GGT ATC ATT CCA AAG GAA ATC GCT AAA GTA TTT TTC CAG CGT AAA           1440
Gly Ile Ile Pro Lys Glu Ile Ala Lys Val Phe Phe Gln Arg Lys
            470                 475                 480

GAC TGG AAA AAG AAA ATG TTC GCT GAA GAA ATG AAT GCC GAA GCT           1485
Asp Trp Lys Lys Lys Met Phe Ala Glu Glu Met Asn Ala Glu Ala
            485                 490                 495

ATT AAA AAG ATT ATT ATG AAA GGC GCA GGG TCT TGT TCA ACT AAA           1530
Ile Lys Lys Ile Ile Met Lys Gly Ala Gly Ser Cys Ser Thr Lys
            500                 505                 510

CCA GAA GTT GAA CGA TAT GTT AAG TTC AGT GAT GAT TTC TTA AAT           1575
Pro Glu Val Glu Arg Tyr Val Lys Phe Ser Asp Asp Phe Leu Asn
            515                 520                 525

GAA CTA TCG AAT TAC ACC GAA TCT GTT CTC AAT AGT CTG ATT GAA           1620
Glu Leu Ser Asn Tyr Thr Glu Ser Val Leu Asn Ser Leu Ile Glu
            530                 535                 540

GAA TGT GAA AAA GCA GCT ACA CTT GCT AAT ACA AAT CAG CTG AAC           1665
Glu Cys Glu Lys Ala Ala Thr Leu Ala Asn Thr Asn Gln Leu Asn
            545                 550                 555

CGT AAA ATT CTC ATT AAC AGT CTT TAT GGT GCT CTT GGT AAT ATT           1710
Arg Lys Ile Leu Ile Asn Ser Leu Tyr Gly Ala Leu Gly Asn Ile
            560                 565                 570

CAT TTC CGT TAC TAT GAT TTG CGA AAT GCT ACT GCT ATC ACA ATT           1755
His Phe Arg Tyr Tyr Asp Leu Arg Asn Ala Thr Ala Ile Thr Ile
            575                 580                 585

TTC GGC CAA GTC GGT ATT CAG TGG ATT GCT CGT AAA ATT AAT GAA           1800
Phe Gly Gln Val Gly Ile Gln Trp Ile Ala Arg Lys Ile Asn Glu
            590                 595                 600

TAT CTG AAT AAA GTA TGC GGA ACT AAT GAT GAA GAT TTC ATT GCA           1845
Tyr Leu Asn Lys Val Cys Gly Thr Asn Asp Glu Asp Phe Ile Ala
            605                 610                 615

GCA GGT GAT ACT GAT TCG GTA TAT GTT TGC GTA GAT AAA GTT ATT           1890
Ala Gly Asp Thr Asp Ser Val Tyr Val Cys Val Asp Lys Val Ile
            620                 625                 630

GAA AAA GTT GGT CTT GAC CGA TTC AAA GAG CAG AAC GAT TTG GTT           1935
Glu Lys Val Gly Leu Asp Arg Phe Lys Glu Gln Asn Asp Leu Val
            635                 640                 645

GAA TTC ATG AAT CAG TTC GGT AAG AAA AAG ATG GAA CCT ATG ATT           1980
Glu Phe Met Asn Gln Phe Gly Lys Lys Lys Met Glu Pro Met Ile
            650                 655                 660

GAT GTT GCA TAT CGT GAG TTA TGT GAT TAT ATG AAT AAC CGC GAG           2025
Asp Val Ala Tyr Arg Glu Leu Cys Asp Tyr Met Asn Asn Arg Glu
            665                 670                 675

CAT CTG ATG CAT ATG GAC CGT GAA GCT ATT TCT TGC CCT CCG CTT           2070
His Leu Met His Met Asp Arg Glu Ala Ile Ser Cys Pro Pro Leu
            680                 685                 690

GGT TCA AAG GGC GTT GGT GGA TTT TGG AAA GCG AAA AAG CGT TAT           2115
Gly Ser Lys Gly Val Gly Gly Phe Trp Lys Ala Lys Lys Arg Tyr
            695                 700                 705

GCT CTG AAC GTT TAT GAT ATG GAA GAT AAG CGA TTT GCT GAA CCG           2160
Ala Leu Asn Val Tyr Asp Met Glu Asp Lys Arg Phe Ala Glu Pro
            710                 715                 720

CAT CTA AAA ATC ATG GGT ATG GAA ACT CAG CAG AGT TCA ACA CCA           2205
His Leu Lys Ile Met Gly Met Glu Thr Gln Gln Ser Ser Thr Pro
            725                 730                 735

AAA GCA GTG CAA GAA GCT CTC GAA GAA AGT ATT CGT CGT ATT CTT           2250
Lys Ala Val Gln Glu Ala Leu Glu Glu Ser Ile Arg Arg Ile Leu
            740                 745                 750

CAG GAA GGT GAA GAG TCT GTC CAA GAA TAC TAC AAG AAC TTC GAG           2295
```

```
Gln Glu Gly Glu Glu Ser Val Gln Glu Tyr Tyr Lys Asn Phe Glu
            755                 760                 765

AAA GAA TAT CGT CAA CTT GAC TAT AAA GTT ATT GCT GAA GTA AAA    2340
Lys Glu Tyr Arg Gln Leu Asp Tyr Lys Val Ile Ala Glu Val Lys
            770                 775                 780

ACT GCG AAC GAT ATA GCG AAA TAT GAT GAT AAA GGT TGG CCA GGA    2385
Thr Ala Asn Asp Ile Ala Lys Tyr Asp Asp Lys Gly Trp Pro Gly
            785                 790                 795

TTT AAA TGC CCG TTC CAT ATT CGT GGT GTA CTA ACT TAT CGT CGA    2430
Phe Lys Cys Pro Phe His Ile Arg Gly Val Leu Thr Tyr Arg Arg
            800                 805                 810

GCT GTT AGC GGT TTA GGT GTA GCT CCA ATT TTG GAT GGA AAT AAA    2475
Ala Val Ser Gly Leu Gly Val Ala Pro Ile Leu Asp Gly Asn Lys
            815                 820                 825

GTA ATG GTT CTT CCA TTA CGT GAA GGA AAT CCA TTT GGT GAC AAG    2520
Val Met Val Leu Pro Leu Arg Glu Gly Asn Pro Phe Gly Asp Lys
            830                 835                 840

TGC ATT GCT TGG CCA TCG GGT ACA GAA CTT CCA AAA GAA ATT CGT    2565
Cys Ile Ala Trp Pro Ser Gly Thr Glu Leu Pro Lys Glu Ile Arg
            845                 850                 855

TCT GAT GTG CTA TCT TGG ATT GAC CAC TCA ACT TTG TTC CAA AAA    2610
Ser Asp Val Leu Ser Trp Ile Asp His Ser Thr Leu Phe Gln Lys
            860                 865                 870

TCG TTT GTT AAA CCG CTT GCG GGT ATG TGT GAA TCG GCT GGC ATG    2655
Ser Phe Val Lys Pro Leu Ala Gly Met Cys Glu Ser Ala Gly Met
            875                 880                 885

GAC TAT GAA GAA AAA GCT TCG TTA GAC TTC CTG TTT GGC                2694
Asp Tyr Glu Glu Lys Ala Ser Leu Asp Phe Leu Phe Gly
            890                 895         898

(2) INFORMATION FOR SEQ ID NO:4:

(i) SEQUENCE CHARACTERISTICS:
        (A) LENGTH: 898 amino acids
        (B) TYPE: amino acid
        (D) TOPOLOGY: linear (ii) MOLECULE TYPE: protein (xi) SEQUENCE DESCRIPTION: SEQ ID NO:4:

Met Lys Glu Phe Tyr Ile Ser Ile Glu Thr Val Gly Asn Asn Ile
                5                   10                  15

Val Glu Arg Tyr Ile Asp Glu Asn Gly Lys Glu Arg Thr Arg Glu
                20                  25                  30

Val Glu Tyr Leu Pro Thr Met Phe Arg His Cys Lys Glu Glu Ser
                35                  40                  45

Lys Tyr Lys Asp Ile Tyr Gly Lys Asn Cys Ala Pro Gln Lys Phe
                50                  55                  60

Pro Ser Met Lys Asp Ala Arg Asp Trp Met Lys Arg Met Glu Asp
                65                  70                  75

Ile Gly Leu Glu Ala Leu Gly Met Asn Asp Phe Lys Leu Ala Tyr
                80                  85                  90

Ile Ser Asp Thr Tyr Gly Ser Glu Ile Val Tyr Asp Arg Lys Phe
                95                  100                 105

Val Arg Val Ala Asn Cys Asp Ile Glu Val Thr Gly Asp Lys Phe
                110                 115                 120

Pro Asp Pro Met Lys Ala Glu Tyr Glu Ile Asp Ala Ile Thr His
                125                 130                 135

Tyr Asp Ser Ile Asp Asp Arg Phe Tyr Val Phe Asp Leu Leu Asn
                140                 145                 150
```

-continued

```
Ser Met Tyr Gly Ser Val Ser Lys Trp Asp Ala Lys Leu Ala Ala
                155                 160                 165
Lys Leu Asp Cys Glu Gly Gly Asp Glu Val Pro Gln Glu Ile Leu
            170                 175                 180
Asp Arg Val Ile Tyr Met Pro Phe Asp Asn Glu Arg Asp Met Leu
        185                 190                 195
Met Glu Tyr Ile Asn Leu Trp Glu Gln Lys Arg Pro Ala Ile Phe
    200                 205                 210
Thr Gly Trp Asn Ile Glu Gly Phe Asp Val Pro Tyr Ile Met Asn
215                 220                 225
Arg Val Lys Met Ile Leu Gly Glu Arg Ser Met Lys Arg Phe Ser
        230                 235                 240
Pro Ile Gly Arg Val Lys Ser Lys Leu Ile Gln Asn Met Tyr Gly
            245                 250                 255
Ser Lys Glu Ile Tyr Ser Ile Asp Gly Val Ser Ile Leu Asp Tyr
                260                 265                 270
Leu Asp Leu Tyr Lys Lys Phe Ala Phe Thr Asn Leu Pro Ser Phe
                    275                 280                 285
Ser Leu Glu Ser Val Ala Gln His Glu Thr Lys Lys Gly Lys Leu
                        290                 295                 300
Pro Tyr Asp Gly Pro Ile Asn Lys Leu Arg Glu Thr Asn His Gln
                            305                 310                 315
Arg Tyr Ile Ser Tyr Asn Ile Ile Asp Val Glu Ser Val Gln Ala
                                320                 325                 330
Ile Asp Lys Ile Arg Gly Phe Ile Asp Leu Val Leu Ser Met Ser
                            335                 340                 345
Tyr Tyr Ala Lys Met Pro Phe Ser Gly Val Met Ser Pro Ile Lys
                        350                 355                 360
Thr Trp Asp Ala Ile Ile Phe Asn Ser Leu Lys Gly Glu His Lys
                    365                 370                 375
Val Ile Pro Gln Gln Gly Ser His Val Lys Gln Ser Phe Pro Gly
                380                 385                 390
Ala Phe Val Phe Glu Pro Lys Pro Ile Ala Arg Arg Tyr Ile Met
            395                 400                 405
Ser Phe Asp Leu Thr Ser Leu Tyr Pro Ser Ile Ile Arg Gln Val
        410                 415                 420
Asn Ile Ser Pro Glu Thr Ile Arg Gly Gln Phe Lys Val His Pro
    425                 430                 435
Ile His Glu Tyr Ile Ala Gly Thr Ala Pro Lys Pro Ser Asp Glu
440                 445                 450
Tyr Ser Cys Ser Pro Asn Gly Trp Met Tyr Asp Lys His Gln Glu
        455                 460                 465
Gly Ile Ile Pro Lys Glu Ile Ala Lys Val Phe Phe Gln Arg Lys
            470                 475                 480
Asp Trp Lys Lys Lys Met Phe Ala Glu Glu Met Asn Ala Glu Ala
                485                 490                 495
Ile Lys Lys Ile Ile Met Lys Gly Ala Gly Ser Cys Ser Thr Lys
                    500                 505                 510
Pro Glu Val Glu Arg Tyr Val Lys Phe Ser Asp Asp Phe Leu Asn
                        515                 520                 525
Glu Leu Ser Asn Tyr Thr Glu Ser Val Leu Asn Ser Leu Ile Glu
                            530                 535                 540
Glu Cys Glu Lys Ala Ala Thr Leu Ala Asn Thr Asn Gln Leu Asn
```

```
                    545                 550                 555
Arg Lys Ile Leu Ile Asn Ser Leu Tyr Gly Ala Leu Gly Asn Ile
                560                 565                 570
His Phe Arg Tyr Tyr Asp Leu Arg Asn Ala Thr Ala Ile Thr Ile
                575                 580                 585
Phe Gly Gln Val Gly Ile Gln Trp Ile Ala Arg Lys Ile Asn Glu
                590                 595                 600
Tyr Leu Asn Lys Val Cys Gly Thr Asn Asp Glu Asp Phe Ile Ala
                605                 610                 615
Ala Gly Asp Thr Asp Ser Val Tyr Val Cys Val Asp Lys Val Ile
                620                 625                 630
Glu Lys Val Gly Leu Asp Arg Phe Lys Glu Gln Asn Asp Leu Val
                635                 640                 645
Glu Phe Met Asn Gln Phe Gly Lys Lys Met Glu Pro Met Ile
                650                 655                 660
Asp Val Ala Tyr Arg Glu Leu Cys Asp Tyr Met Asn Asn Arg Glu
                665                 670                 675
His Leu Met His Met Asp Arg Glu Ala Ile Ser Cys Pro Pro Leu
                680                 685                 690
Gly Ser Lys Gly Val Gly Gly Phe Trp Lys Ala Lys Lys Arg Tyr
                695                 700                 705
Ala Leu Asn Val Tyr Asp Met Glu Asp Lys Arg Phe Ala Glu Pro
                710                 715                 720
His Leu Lys Ile Met Gly Met Glu Thr Gln Gln Ser Ser Thr Pro
                725                 730                 735
Lys Ala Val Gln Glu Ala Leu Glu Glu Ser Ile Arg Arg Ile Leu
                740                 745                 750
Gln Glu Gly Glu Glu Ser Val Gln Glu Tyr Tyr Lys Asn Phe Glu
                755                 760                 765
Lys Glu Tyr Arg Gln Leu Asp Tyr Lys Val Ile Ala Glu Val Lys
                770                 775                 780
Thr Ala Asn Asp Ile Ala Lys Tyr Asp Asp Lys Gly Trp Pro Gly
                785                 790                 795
Phe Lys Cys Pro Phe His Ile Arg Gly Val Leu Thr Tyr Arg Arg
                800                 805                 810
Ala Val Ser Gly Leu Gly Val Ala Pro Ile Leu Asp Gly Asn Lys
                815                 820                 825
Val Met Val Leu Pro Leu Arg Glu Gly Asn Pro Phe Gly Asp Lys
                830                 835                 840
Cys Ile Ala Trp Pro Ser Gly Thr Glu Leu Pro Lys Glu Ile Arg
                845                 850                 855
Ser Asp Val Leu Ser Trp Ile Asp His Ser Thr Leu Phe Gln Lys
                860                 865                 870
Ser Phe Val Lys Pro Leu Ala Gly Met Cys Glu Ser Ala Gly Met
                875                 880                 885
Asp Tyr Glu Glu Lys Ala Ser Leu Asp Phe Leu Phe Gly
                890                 895             898

(2) INFORMATION FOR SEQ ID NO:5:

(i) SEQUENCE CHARACTERISTICS:
        (A) LENGTH: 2459 base pairs
        (B) TYPE: nucleic acid
        (C) STRANDEDNESS: single
        (D) TOPOLOGY: linear
```

(ii) MOLECULE TYPE: DNA (genomic)

(ix) FEATURE:
   (A) NAME/KEY: CDS
   (B) LOCATION: 108..2456

(xi) SEQUENCE DESCRIPTION: SEQ ID NO:5:

```
AAGCATGGCG CGAAGGCATA TTACGGGCAG TAATGACTGT ATAAAACCAC            50

AGCCAATCAA ACGAAACCAG GCTATACTCA AGCCTGGTTT TTTGATGGAT           100

TTTCAGC GTG GCG CAG GCA GGT TTT ATC TTA ACC CGA                  137
        Val Ala Gln Ala Gly Phe Ile Leu Thr Arg
                      5                      10

CAC TGG CGG GAC ACC CCG CAA GGG ACA GAA GTC TCC TTC TGG CTG      182
His Trp Arg Asp Thr Pro Gln Gly Thr Glu Val Ser Phe Trp Leu
            15                  20                  25

GCG ACG GAC AAC GGG CCG TTG CAG GTT ACG CTT GCA CCG CAA GAG      227
Ala Thr Asp Asn Gly Pro Leu Gln Val Thr Leu Ala Pro Gln Glu
                30                  35                  40

TCC GTG GCG TTT ATT CCC GCC GAT CAG GTT CCC CGC GCT CAG CAT      272
Ser Val Ala Phe Ile Pro Ala Asp Gln Val Pro Arg Ala Gln His
            45                  50                  55

ATT TTG CAG GGT GAA CAA GGC TTT CGC CTG ACA CCG CTG GCG TTA      317
Ile Leu Gln Gly Glu Gln Gly Phe Arg Leu Thr Pro Leu Ala Leu
                60                  65                  70

AAG GAT TTT CAC CGC CAG CCG GTG TAT GGC CTT TAC TGT CGC GCC      362
Lys Asp Phe His Arg Gln Pro Val Tyr Gly Leu Tyr Cys Arg Ala
            75                  80                  85

CAT CGC CAA TTG ATG AAT TAC GAA AAG CGC CTG CGT GAA GGT GGC      407
His Arg Gln Leu Met Asn Tyr Glu Lys Arg Leu Arg Glu Gly Gly
                90                  95                 100

GTT ACC GTC TAC GAG GCC GAT GTG CGT CCG CCA GAA CGC TAT CTG      452
Val Thr Val Tyr Glu Ala Asp Val Arg Pro Pro Glu Arg Tyr Leu
            105                 110                 115

ATG GAG CGG TTT ATC ACC TCA CCG GTG TGG GTC GAG GGT GAT ATG      497
Met Glu Arg Phe Ile Thr Ser Pro Val Trp Val Glu Gly Asp Met
                120                 125                 130

CAC AAT GGC ACT ATC GTT AAT GCC CGT CTG AAA CCG CAT CCC GAC      542
His Asn Gly Thr Ile Val Asn Ala Arg Leu Lys Pro His Pro Asp
            135                 140                 145

TAT CGT CCG CCG CTC AAG TGG GTT TCT ATA GAT ATT GAA ACC ACC      587
Tyr Arg Pro Pro Leu Lys Trp Val Ser Ile Asp Ile Glu Thr Thr
                150                 155                 160

CGC CAC GGT GAG CTG TAC TGC ATC GGC CTG GAA GGC TGC GGG CAG      632
Arg His Gly Glu Leu Tyr Cys Ile Gly Leu Glu Gly Cys Gly Gln
            165                 170                 175

CGC ATC GTT TAT ATG CTG GGG CCG GAG AAT GGC GAC GCC TCC TCG      677
Arg Ile Val Tyr Met Leu Gly Pro Glu Asn Gly Asp Ala Ser Ser
                180                 185                 190

CTT GAT TTC GAA CTG GAA TAC GTC GCC AGC CGC CCG CAG TTG CTG      722
Leu Asp Phe Glu Leu Glu Tyr Val Ala Ser Arg Pro Gln Leu Leu
            195                 200                 205

GAA AAA CTC AAC GCC TGG TTT GCC AAC TAC GAT CCT GAT GTG ATC      767
Glu Lys Leu Asn Ala Trp Phe Ala Asn Tyr Asp Pro Asp Val Ile
                210                 215                 220

ATC GGT TGG AAC GTG GTG CAG TTC GAT CTG CGA ATG CTG CAA AAA      812
Ile Gly Trp Asn Val Val Gln Phe Asp Leu Arg Met Leu Gln Lys
            225                 230                 235

CAT GCC GAG CGT TAC CGT CTT CCG CTG CGT CTT GGG CGC GAT AAT      857
His Ala Glu Arg Tyr Arg Leu Pro Leu Arg Leu Gly Arg Asp Asn
                240                 245                 250
```

```
AGC GAG CTG GAG TGG CGC GAC GAC GGC TTT AAA AAC GGC GTC TTT    902
Ser Glu Leu Glu Trp Arg Asp Asp Gly Phe Lys Asn Gly Val Phe
            255                 260                 265

TTT GCC CAG GCT AAA GGT GGG CTA ATT ATC GAC GGT ATC GAG GCG    947
Phe Ala Gln Ala Lys Gly Gly Leu Ile Ile Asp Gly Ile Glu Ala
            270                 275                 280

CTG AAA TCC GCG TTC TGG AAT TTC TCT TCA TTC TCG CTG GAA ACT    992
Leu Lys Ser Ala Phe Trp Asn Phe Ser Ser Phe Ser Leu Glu Thr
            285                 290                 295

GTC GCT CAG GAG CTA TTA GGC GAA GGA AAA TCT ATC GAT AAC CCG   1037
Val Ala Gln Glu Leu Leu Gly Glu Gly Lys Ser Ile Asp Asn Pro
            300                 305                 310

TGG GAT CGA ATG GAC GAA ATT GAC CGC CGT TTC GCC GAA GAT AAA   1082
Trp Asp Arg Met Asp Glu Ile Asp Arg Arg Phe Ala Glu Asp Lys
            315                 320                 325

CCT GCG CTG GCA ACT TAT AAC CTG AAA GAT TGC GAG CTG GTG ACG   1127
Pro Ala Leu Ala Thr Tyr Asn Leu Lys Asp Cys Glu Leu Val Thr
            330                 335                 340

CAG ATC TTC CAC AAA ACT GAA ATC ATG CCA TTT TTA CTC GAA CGG   1172
Gln Ile Phe His Lys Thr Glu Ile Met Pro Phe Leu Leu Glu Arg
            345                 350                 355

GCA ACG GTG AAC GGC CTG CCG GTG GAC CGA CAC GGC GGT TCG GTG   1217
Ala Thr Val Asn Gly Leu Pro Val Asp Arg His Gly Gly Ser Val
            360                 365                 370

GCG GCA TTT GGT CAT CTC TAT TTT CCG CGA ATG CAT CGC GCT GGT   1262
Ala Ala Phe Gly His Leu Tyr Phe Pro Arg Met His Arg Ala Gly
            375                 380                 385

TAT GTC GCG CCT AAT CTC GGC GAA GTG CCG CCG CAC GCC AGC CCT   1307
Tyr Val Ala Pro Asn Leu Gly Glu Val Pro Pro His Ala Ser Pro
            390                 395                 400

GGC GGC TAC GTG ATG GAT TCA CGG CCA GGG CTT TAT GAT TCA GTG   1352
Gly Gly Tyr Val Met Asp Ser Arg Pro Gly Leu Tyr Asp Ser Val
            405                 410                 415

CTG GTG CTG GAC TAT AAA AGC CTG TAC CCG TCG ATC ATC CGC ACC   1397
Leu Val Leu Asp Tyr Lys Ser Leu Tyr Pro Ser Ile Ile Arg Thr
            420                 425                 430

TTT CTG ATT GAT CCC GTC GGG CTG GTG GAA GGC ATG GCG CAG CCT   1442
Phe Leu Ile Asp Pro Val Gly Leu Val Glu Gly Met Ala Gln Pro
            435                 440                 445

GAT CCA GAG CAC AGT ACC GAA GGT TTT CTC GAT GCC TGG TTC TCG   1487
Asp Pro Glu His Ser Thr Glu Gly Phe Leu Asp Ala Trp Phe Ser
            450                 455                 460

CGA GAA AAA CAT TGC CTG CCG GAG ATT GTG ACT AAC ATC TGG CAC   1532
Arg Glu Lys His Cys Leu Pro Glu Ile Val Thr Asn Ile Trp His
            465                 470                 475

GGG CGC GAT GAA GCC AAA CGC CAG GGT AAC AAA CCG CTG TCG CAG   1577
Gly Arg Asp Glu Ala Lys Arg Gln Gly Asn Lys Pro Leu Ser Gln
            480                 485                 490

GCG CTG AAA ATC ATC ATG AAT GCC TTT TAT GGC GTG CTC GGC ACC   1622
Ala Leu Lys Ile Ile Met Asn Ala Phe Tyr Gly Val Leu Gly Thr
            495                 500                 505

ACC GCC TGC CGC TTC TTC GAT CCG CGG CTG GCA TCG TCG ATC ACC   1667
Thr Ala Cys Arg Phe Phe Asp Pro Arg Leu Ala Ser Ser Ile Thr
            510                 515                 520

ATG CGT GGT CAT CAG ATC ATG CGG CAA ACC AAA GCG TTG ATT GAA   1712
Met Arg Gly His Gln Ile Met Arg Gln Thr Lys Ala Leu Ile Glu
            525                 530                 535

GCA CAG GGC TAC GAC GTT ATC TAC GGC GAT ACC GAC TCA ACG TTT   1757
Ala Gln Gly Tyr Asp Val Ile Tyr Gly Asp Thr Asp Ser Thr Phe
            540                 545                 550
```

```
GTC TGG CTG AAA GGC GCA CAT TCG GAA GAA GAA GCG GCG AAA ATC    1802
Val Trp Leu Lys Gly Ala His Ser Glu Glu Glu Ala Ala Lys Ile
                555                 560                 565

GGT CGT GCA CTG GTG CAG CAC GTT AAC GCC TGG TGG GCG GAA ACG    1847
Gly Arg Ala Leu Val Gln His Val Asn Ala Trp Trp Ala Glu Thr
                570                 575                 580

CTG CAA AAA CAA CGG CTG ACC AGC GCA TTA GAA CTG GAG TAT GAA    1892
Leu Gln Lys Gln Arg Leu Thr Ser Ala Leu Glu Leu Glu Tyr Glu
                585                 590                 595

ACC CAT TTC TGC CGT TTT CTG ATG CCA ACC ATT CGC GGA GCC GAT    1937
Thr His Phe Cys Arg Phe Leu Met Pro Thr Ile Arg Gly Ala Asp
                600                 605                 610

ACC GGC AGT AAA AAG CGT TAT GCC GGA CTG ATT CAG GAG GGC GAC    1982
Thr Gly Ser Lys Lys Arg Tyr Ala Gly Leu Ile Gln Glu Gly Asp
                615                 620                 625

AAG CAG CGG ATG GTG TTT AAA GGG CTG GAA ACC GTG CGC ACC GAC    2027
Lys Gln Arg Met Val Phe Lys Gly Leu Glu Thr Val Arg Thr Asp
                630                 635                 640

TGG ACG CCG CTG GCC CAG CAG TTT CAG CAG GAG CTA TAC CTG CGC    2072
Trp Thr Pro Leu Ala Gln Gln Phe Gln Gln Glu Leu Tyr Leu Arg
                645                 650                 655

ATC TTC CGC AAC GAG CCA TAT CAG GAA TAT GTA CGC GAA ACC ATC    2117
Ile Phe Arg Asn Glu Pro Tyr Gln Glu Tyr Val Arg Glu Thr Ile
                660                 665                 670

GAC AAA CTG ATG GCG GGT GAA CTG GAT GCG CGA CTG GTT TAC CGT    2162
Asp Lys Leu Met Ala Gly Glu Leu Asp Ala Arg Leu Val Tyr Arg
                675                 680                 685

AAA CGC CTT CGC CGT CCG CTG AGC GAG TAT CAG CGT AAT GTG CCG    2207
Lys Arg Leu Arg Arg Pro Leu Ser Glu Tyr Gln Arg Asn Val Pro
                690                 695                 700

CCT CAT GTA CGC GCC GCT CGC CTT GCC GAT GAA GAA AAC CAA AAG    2252
Pro His Val Arg Ala Ala Arg Leu Ala Asp Glu Glu Asn Gln Lys
                705                 710                 715

CGT GGT CGC CCC TTG CAA TAT CAG AAT CGC GGC ACC ATT AAG TAC    2297
Arg Gly Arg Pro Leu Gln Tyr Gln Asn Arg Gly Thr Ile Lys Tyr
                720                 725                 730

GTA TGG ACC ACC AAC GGC CCG GAG CCG CTG GAC TAC CAA CGT TCA    2342
Val Trp Thr Thr Asn Gly Pro Glu Pro Leu Asp Tyr Gln Arg Ser
                735                 740                 745

CCA CTG GAT TAC GAA CAC TAT CTG ACC CGC CAG CTA CAA CCC GTG    2387
Pro Leu Asp Tyr Glu His Tyr Leu Thr Arg Gln Leu Gln Pro Val
                750                 755                 760

GCG GAG GGA ATA CTC CCT TTT ATT GAG GAT AAT TTT GCT ACA CTT    2432
Ala Glu Gly Ile Leu Pro Phe Ile Glu Asp Asn Phe Ala Thr Leu
                765                 770                 775

ATG ACC GGG CAA CTT GGG CTA TTT TGA                            2459
Met Thr Gly Gln Leu Gly Leu Phe
                780         783

(2) INFORMATION FOR SEQ ID NO:6:

(i) SEQUENCE CHARACTERISTICS:
        (A) LENGTH: 783 base pairs
        (B) TYPE: amino acid
        (D) TOPOLOGY: linear (ii) MOLECULE TYPE: protein (xi) SEQUENCE DESCRIPTION: SEQ ID NO:6:

Val Ala Gln Ala Gly Phe Ile Leu Thr Arg His Trp Arg Asp Thr
                  5                 10                  15

Pro Gln Gly Thr Glu Val Ser Phe Trp Leu Ala Thr Asp Asn Gly
```

-continued

```
                    20                  25                  30
Pro Leu Gln Val Thr Leu Ala Pro Gln Glu Ser Val Ala Phe Ile
                    35                  40                  45
Pro Ala Asp Gln Val Pro Arg Ala Gln His Ile Leu Gln Gly Glu
                    50                  55                  60
Gln Gly Phe Arg Leu Thr Pro Leu Ala Leu Lys Asp Phe His Arg
                    65                  70                  75
Gln Pro Val Tyr Gly Leu Tyr Cys Arg Ala His Arg Gln Leu Met
                    80                  85                  90
Asn Tyr Glu Lys Arg Leu Arg Glu Gly Val Thr Val Tyr Glu
                    95                 100                 105
Ala Asp Val Arg Pro Pro Glu Arg Tyr Leu Met Glu Arg Phe Ile
                   110                 115                 120
Thr Ser Pro Val Trp Val Glu Gly Asp Met His Asn Gly Thr Ile
                   125                 130                 135
Val Asn Ala Arg Leu Lys Pro His Pro Asp Tyr Arg Pro Pro Leu
                   140                 145                 150
Lys Trp Val Ser Ile Asp Ile Glu Thr Thr Arg His Gly Glu Leu
                   155                 160                 165
Tyr Cys Ile Gly Leu Glu Gly Cys Gly Gln Arg Ile Val Tyr Met
                   170                 175                 180
Leu Gly Pro Glu Asn Gly Asp Ala Ser Ser Leu Asp Phe Glu Leu
                   185                 190                 195
Glu Tyr Val Ala Ser Arg Pro Gln Leu Leu Glu Lys Leu Asn Ala
                   200                 205                 210
Trp Phe Ala Asn Tyr Asp Pro Asp Val Ile Ile Gly Trp Asn Val
                   215                 220                 225
Val Gln Phe Asp Leu Arg Met Leu Gln Lys His Ala Glu Arg Tyr
                   230                 235                 240
Arg Leu Pro Leu Arg Leu Gly Arg Asp Asn Ser Glu Leu Glu Trp
                   245                 250                 255
Arg Asp Asp Gly Phe Lys Asn Gly Val Phe Phe Ala Gln Ala Lys
                   260                 265                 270
Gly Gly Leu Ile Ile Asp Gly Ile Glu Ala Leu Lys Ser Ala Phe
                   275                 280                 285
Trp Asn Phe Ser Ser Phe Ser Leu Glu Thr Val Ala Gln Glu Leu
                   290                 295                 300
Leu Gly Glu Gly Lys Ser Ile Asp Asn Pro Trp Asp Arg Met Asp
                   305                 310                 315
Glu Ile Asp Arg Arg Phe Ala Glu Asp Lys Pro Ala Leu Ala Thr
                   320                 325                 330
Tyr Asn Leu Lys Asp Cys Glu Leu Val Thr Gln Ile Phe His Lys
                   335                 340                 345
Thr Glu Ile Met Pro Phe Leu Leu Glu Arg Ala Thr Val Asn Gly
                   350                 355                 360
Leu Pro Val Asp Arg His Gly Gly Ser Val Ala Ala Phe Gly His
                   365                 370                 375
Leu Tyr Phe Pro Arg Met His Arg Ala Gly Tyr Val Ala Pro Asn
                   380                 385                 390
Leu Gly Glu Val Pro Pro His Ala Ser Pro Gly Gly Tyr Val Met
                   395                 400                 405
Asp Ser Arg Pro Gly Leu Tyr Asp Ser Val Leu Val Leu Asp Tyr
                   410                 415                 420
```

```
Lys Ser Leu Tyr Pro Ser Ile Ile Arg Thr Phe Leu Ile Asp Pro
                425                 430                 435

Val Gly Leu Val Glu Gly Met Ala Gln Pro Asp Pro Glu His Ser
                440                 445                 450

Thr Glu Gly Phe Leu Asp Ala Trp Phe Ser Arg Glu Lys His Cys
                455                 460                 465

Leu Pro Glu Ile Val Thr Asn Ile Trp His Gly Arg Asp Glu Ala
                470                 475                 480

Lys Arg Gln Gly Asn Lys Pro Leu Ser Gln Ala Leu Lys Ile Ile
                485                 490                 495

Met Asn Ala Phe Tyr Gly Val Leu Gly Thr Thr Ala Cys Arg Phe
                500                 505                 510

Phe Asp Pro Arg Leu Ala Ser Ser Ile Thr Met Arg Gly His Gln
                515                 520                 525

Ile Met Arg Gln Thr Lys Ala Leu Ile Glu Ala Gln Gly Tyr Asp
                530                 535                 540

Val Ile Tyr Gly Asp Thr Asp Ser Thr Phe Val Trp Leu Lys Gly
                545                 550                 555

Ala His Ser Glu Glu Ala Ala Lys Ile Gly Arg Ala Leu Val
                560                 565                 570

Gln His Val Asn Ala Trp Trp Ala Glu Thr Leu Gln Lys Gln Arg
                575                 580                 585

Leu Thr Ser Ala Leu Glu Leu Glu Tyr Glu Thr His Phe Cys Arg
                590                 595                 600

Phe Leu Met Pro Thr Ile Arg Gly Ala Asp Thr Gly Ser Lys Lys
                605                 610                 615

Arg Tyr Ala Gly Leu Ile Gln Glu Gly Asp Lys Gln Arg Met Val
                620                 625                 630

Phe Lys Gly Leu Glu Thr Val Arg Thr Asp Trp Thr Pro Leu Ala
                635                 640                 645

Gln Gln Phe Gln Gln Glu Leu Tyr Leu Arg Ile Phe Arg Asn Glu
                650                 655                 660

Pro Tyr Gln Glu Tyr Val Arg Glu Thr Ile Asp Lys Leu Met Ala
                665                 670                 675

Gly Glu Leu Asp Ala Arg Leu Val Tyr Arg Lys Arg Leu Arg Arg
                680                 685                 690

Pro Leu Ser Glu Tyr Gln Arg Asn Val Pro Pro His Val Arg Ala
                695                 700                 705

Ala Arg Leu Ala Asp Glu Glu Asn Gln Lys Arg Gly Arg Pro Leu
                710                 715                 720

Gln Tyr Gln Asn Arg Gly Thr Ile Lys Tyr Val Trp Thr Thr Asn
                725                 730                 735

Gly Pro Glu Pro Leu Asp Tyr Gln Arg Ser Pro Leu Asp Tyr Glu
                740                 745                 750

His Tyr Leu Thr Arg Gln Leu Gln Pro Val Ala Glu Gly Ile Leu
                755                 760                 765

Pro Phe Ile Glu Asp Asn Phe Ala Thr Leu Met Thr Gly Gln Leu
                770                 775                 780

Gly Leu Phe
        783
```